United States Patent
Giambattista et al.

(10) Patent No.: US 7,314,464 B2
(45) Date of Patent: *Jan. 1, 2008

(54) PEN NEEDLE AND SAFETY SYSTEM

(75) Inventors: Lucio Giambattista, East Hanover, NJ (US); David De Salvo, Butler, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/205,919

(22) Filed: Aug. 17, 2005

(65) Prior Publication Data

US 2005/0277895 A1  Dec. 15, 2005

Related U.S. Application Data

(63) Continuation of application No. 10/191,714, filed on Jul. 9, 2002, now Pat. No. 6,986,760, which is a continuation-in-part of application No. 10/072,691, filed on Feb. 7, 2002, now abandoned.

(60) Provisional application No. 60/222,454, filed on Aug. 2, 2000.

(51) Int. Cl.
    *A61M 5/32* (2006.01)
(52) U.S. Cl. ............ 604/198; 604/110; 604/192; 604/263
(58) Field of Classification Search .......... 604/110, 604/198, 263, 192, 195
    See application file for complete search history.

(56) References Cited

U.S. PATENT DOCUMENTS

| 2,752,918 A | 7/1956 | Uytenbogaart |
| 3,712,301 A | 1/1973 | Sarnoff |
| 3,882,863 A | 5/1975 | Sarnoff et al. |
| 4,031,893 A | 6/1977 | Kaplan et al. |
| 4,214,584 A | 7/1980 | Smirnov et al. |
| 4,226,235 A | 10/1980 | Sarnoff et al. |
| 4,413,760 A | 11/1983 | Paton |
| 4,565,543 A | 1/1986 | Bekkering et al. |
| 4,624,660 A | 11/1986 | Mijers et al. |

(Continued)

FOREIGN PATENT DOCUMENTS

| WO | WO 92/19296 | 12/1992 |
| WO | WO 97/14455 | 4/1997 |
| WO | WO 01/64270 | * 9/2001 |
| WO | WO 02/09797 | 2/2002 |

*Primary Examiner*—Kevin C. Sirmons
*Assistant Examiner*—Andrew Gilbert
(74) *Attorney, Agent, or Firm*—Alan W. Fiedler; Fitzpatrick Cella Harper & Scinto LLP

(57) ABSTRACT

A safety shield system having a needle assembly with a safety shield movable from a first position enclosing an end of a needle cannula, to a second position exposing the end of the needle cannula for injection, to a third position lockingly enclosing the end of a needle cannula. The safety shield system permits retraction of the safety shield during use, but extends the shield enclosing the needle cannula in a locked position following use. The safety shield system also has a cap for receiving the needle assembly and lockingly enclosing another end of the needle cannula. Thus, both ends of a double-ended needle cannula are lockingly enclosed following use of the needle assembly of the inventive safety shield system.

14 Claims, 14 Drawing Sheets

U.S. PATENT DOCUMENTS

| | | |
|---|---|---|
| 4,755,169 A | 7/1988 | Sarnoff et al. |
| 4,822,340 A | 4/1989 | Kamstra |
| 4,894,055 A | 1/1990 | Sudnak |
| 4,968,302 A | 11/1990 | Schluter et al. |
| 5,017,190 A | 5/1991 | Simon et al. |
| 5,085,641 A | 2/1992 | Sarnoff et al. |
| 5,085,642 A | 2/1992 | Sarnoff et al. |
| 5,104,380 A | 4/1992 | Holman et al. |
| 5,112,317 A | 5/1992 | Michel |
| 5,169,392 A | 12/1992 | Ranford et al. |
| 5,201,708 A * | 4/1993 | Martin ............... 604/110 |
| 5,201,721 A | 4/1993 | Lee et al. |
| 5,226,895 A | 7/1993 | Harris |
| 5,226,896 A | 7/1993 | Harris |
| 5,244,465 A | 9/1993 | Michel |
| 5,279,585 A | 1/1994 | Balkwill |
| 5,279,586 A | 1/1994 | Balkwill |
| 5,295,976 A | 3/1994 | Harris |
| 5,300,030 A | 4/1994 | Crossman et al. |
| 5,304,152 A | 4/1994 | Sams |
| D347,894 S | 6/1994 | Hansen et al. ............ D24/129 |
| 5,330,426 A | 7/1994 | Kriesel et al. |
| 5,358,489 A | 10/1994 | Wyrick |
| 5,383,865 A | 1/1995 | Michel |
| 5,385,551 A | 1/1995 | Shaw |
| 5,391,151 A | 2/1995 | Wilmot |
| 5,403,286 A * | 4/1995 | Lockwood, Jr. ............ 604/110 |
| 5,415,645 A | 5/1995 | Friend et al. |
| 5,417,660 A | 5/1995 | Martin |
| 5,417,662 A | 5/1995 | Hjertman et al. |
| 5,423,758 A * | 6/1995 | Shaw ............... 604/110 |
| 5,429,612 A | 7/1995 | Berthier |
| 5,478,316 A | 12/1995 | Bitdinger et al. |
| 5,480,387 A | 1/1996 | Gabriel et al. |
| 5,514,097 A | 5/1996 | Knauer |
| 5,540,664 A | 7/1996 | Wyrick |
| 5,545,145 A | 8/1996 | Clinton et al. |
| 5,549,558 A | 8/1996 | Martin ............... 604/110 |
| 5,569,192 A | 10/1996 | van der Wal |
| 5,584,815 A | 12/1996 | Pawelka et al. |
| 5,593,390 A | 1/1997 | Castellano et al. |
| 5,620,421 A | 4/1997 | Schmitz |
| 5,626,566 A | 5/1997 | Petersen et al. ............ 604/208 |
| 5,634,910 A | 6/1997 | Kanner et al. ............ 604/208 |
| 5,637,094 A | 6/1997 | Stewart, Jr. et al. |
| 5,645,534 A | 7/1997 | Chanoch |
| 5,658,259 A * | 8/1997 | Pearson et al. ............ 604/232 |
| 5,665,071 A | 9/1997 | Wyrick |
| 5,674,203 A | 10/1997 | Lewandowski |
| 5,679,111 A | 10/1997 | Hjertman et al. |
| 5,688,251 A | 11/1997 | Chanoch |
| 5,693,027 A | 12/1997 | Hansen et al. ............ 604/232 |
| 5,695,472 A | 12/1997 | Wyrick |
| 5,709,662 A | 1/1998 | Olive et al. |
| 5,725,508 A | 3/1998 | Chanoch et al. |
| 5,728,074 A | 3/1998 | Castellano et al. |
| 5,746,727 A | 5/1998 | Graves et al. ............ 604/283 |
| 5,820,602 A | 10/1998 | Kovelman et al. |
| 5,827,232 A | 10/1998 | Chanoch et al. |
| 5,829,589 A | 11/1998 | Ngueyn et al. |
| 5,836,911 A | 11/1998 | Marzynski et al. |
| 5,843,036 A | 12/1998 | Olive et al. |
| 5,873,462 A | 2/1999 | Ngueyn et al. |
| 5,873,856 A * | 2/1999 | Hjertman et al. ............ 604/117 |
| 5,893,845 A | 4/1999 | Newby et al. ............ 604/198 |
| 5,928,205 A | 7/1999 | Marshall |
| 5,938,642 A | 8/1999 | Burroughs et al. |
| 5,941,857 A | 8/1999 | Ngueyn et al. |
| 5,944,700 A | 8/1999 | Ngueyn et al. |
| 5,951,530 A | 9/1999 | Steengaard et al. |
| 5,957,896 A | 9/1999 | Bendek et al. |
| 5,961,495 A | 10/1999 | Walters et al. |
| 5,964,731 A | 10/1999 | Kovelman |
| 5,968,021 A | 10/1999 | Ejlersen ............... 604/263 |
| 5,971,966 A | 10/1999 | Lav ............... 604/263 |
| 5,980,491 A | 11/1999 | Hansen |
| 5,984,900 A | 11/1999 | Mikkelsen |
| 5,984,906 A | 11/1999 | Bonnichsen et al. |
| 6,001,082 A | 12/1999 | Dair et al. |
| 6,001,089 A | 12/1999 | Burroughs et al. |
| 6,004,297 A | 12/1999 | Steenfeldt-Jensen et al. ............... 604/207 |
| 6,017,329 A | 1/2000 | Hake |
| 6,039,713 A | 3/2000 | Botich et al. |
| 6,048,336 A | 4/2000 | Gabriel |
| 6,056,728 A | 5/2000 | von Schuckmann |
| 6,077,247 A | 6/2000 | Marshall et al. |
| 6,077,253 A | 6/2000 | Cosme |
| 6,090,080 A | 7/2000 | Jost et al. |
| 6,093,172 A | 7/2000 | Funderburk et al. |
| 6,110,149 A | 8/2000 | Klitgaard et al. ............ 604/209 |
| 6,126,194 A | 10/2000 | Yaniv et al. |
| 6,126,646 A | 10/2000 | Hansen et al. ............ 604/256 |
| 6,159,181 A | 12/2000 | Crossman et al. |
| 6,162,197 A | 12/2000 | Mohammad |
| 6,193,698 B1 | 2/2001 | Kirchhofer et al. |
| 6,203,529 B1 * | 3/2001 | Gabriel et al. ............ 604/192 |
| 6,221,046 B1 | 4/2001 | Burroughs et al. |
| 6,221,053 B1 | 4/2001 | Walters et al. |
| 6,241,709 B1 | 6/2001 | Bechtold et al. |
| 6,248,095 B1 | 6/2001 | Giambattista et al. |
| 6,277,097 B1 | 8/2001 | Mikkelsen et al. |
| 6,277,099 B1 | 8/2001 | Strowe et al. |
| 6,277,101 B1 | 8/2001 | Kirchhofer et al. |
| 6,319,225 B1 | 11/2001 | Sugita et al. ............ 604/89 |
| 6,322,540 B1 | 11/2001 | Grabis et al. |
| 6,379,337 B1 * | 4/2002 | Mohammad M. B. B. S. ............ 604/195 |
| 6,547,764 B2 | 4/2003 | Larsen et al. |
| 6,569,123 B2 | 5/2003 | Alchas et al. |
| 6,773,415 B2 * | 8/2004 | Heiniger ............ 604/110 |
| 6,986,760 B2 * | 1/2006 | Giambattista et al. ............ 604/198 |
| 7,074,211 B1 * | 7/2006 | Heiniger et al. ............ 604/198 |
| 7,104,969 B2 | 9/2006 | Du Plessis |
| 2001/0005781 A1 | 6/2001 | Bergens et al. |
| 2001/0009990 A1 | 7/2001 | Hostettler et al. |
| 2001/0020155 A1 | 9/2001 | Mikkelsen et al. |
| 2001/0051792 A1 | 12/2001 | Kirchhofer et al. |
| 2002/0000468 A1 | 1/2002 | Larsen et al. |
| 2005/0283115 A1 * | 12/2005 | Giambattista et al. ............ 604/110 |

* cited by examiner

PEN NEEDLE AND SAFETY SYSTEM

CROSS-REFERENCE TO RELATED APPLICATIONS

This patent application is a continuation of U.S. application Ser. No. 10/191,714, now U.S. Pat. No. 6,986,760, which is a continuation-in-part of U.S. patent application Ser. No. 10/072,691, now Abandoned, which claims priority to U.S. Provisional Application Ser. No. 60/222,454 Aug. 2, 2000.

FIELD OF THE INVENTION

The present invention is a safety shield system for an injection device comprising a needle assembly and cap which provide for protection of both ends of a double-ended needle cannula after injection using the needle assembly and injection device. As used herein, the term injection device refers to any device which may contain a medicament, in whatever form (e.g., liquid, solid, powder, or combinations thereof), and which may be used to inject such medicament into a patient. As used herein, the term injection device includes sterilized and non-sterilized devices, filled (with medicament) and unfilled devices, and any variation or combination thereof. For example, an injection device may be a pen-type injector which receives a syringe or cartridge, and on which the inventive needle assembly may be provided.

Hypodermic syringes are typically used to deliver selected doses of a medicament to a patient. However, many medicaments are self-administered (e.g., insulin). The manipulation of a hypodermic syringe necessary to carry-out an injection may be difficult and inconvenient, particularly where the injection is self-administered. Medication delivery pens or pen injectors have therefore been developed to facilitate self-administration of injections. Pen injectors may include a generally tubular body portion which is sized and shaped to receive a cartridge carrying a medicament and having a pierceable closure, such as a rubber septum, on one end and a movable stopper-provided at an opposite end and typically inside of the cartridge. A known pen needle may be removably secured to an end of the pen injector. The pen needle includes a hub that carries a double-ended needle cannula and that is configured to be removably secured to the pen injector. The needle cannula has a first end for piercing the closure of the cartridge when the pen needle is secured to the pen injector. The needle cannula also has a second end having a sharpened tip for piercing the skin of a patient during use of the pen injector. The pen needle may also have a removable cap that covers the second end of the needle cannula prior to use.

Safety shield systems have also been developed for hypodermic syringes wherein a tubular shield is moved to enclose the needle cannula and optionally lock in place following injection. Such safety shield systems are typically operated manually or are spring biased to cause the tubular shield to enclose the needle cannula following injection. Syringes equipped with such safety shield systems are typically discarded completely (i.e., syringe and safety shield system) after use. Thus, such safety shield systems are not adaptable for use with pen injectors, which are intended for multiple uses. In addition, such known systems need not contemplate a second end of a needle cannula, as is the case with pen needles. Consequently, prior art safety shield systems, whether for pen injectors or for hypodermic syringes, have various shortcomings.

A safety shield system for pen injectors has not yet been developed wherein a safety shield: initially encloses the tip of the second end or patient end of the needle cannula prior to use; is movable to expose the tip of the second end of the needle cannula to enable the user of the pen injector to pierce the patient's skin; and is movable to lockingly enclose the tip of the second end of the needle cannula after use of the pen injector. In addition, there further exists a need for a safety shield system for pen injectors that provides for protection of the first end of the needle cannula after use of the pen injector. Such a system would shield both the first and second ends of the needle cannula after use, thereby eliminating the possibility of needle stick injury by a user of the needle assembly.

SUMMARY OF THE INVENTION

The safety shield system of the present invention solves the above-described shortcomings of the prior art by providing a needle assembly having a shield that is movable from a first position, in which it encloses and covers the tip of the second or patient end of a double-ended needle cannula, to a second position, in which the tip of the second end of the needle cannula is exposed, to a third position, in which the shield lockingly encloses and covers the tip of the second end of the needle cannula. In addition, the present invention provides a cap that lockingly covers the first end of the needle cannula. Thus, the present invention provides means for lockably shielding both ends of a double-ended needle cannula. The present invention also prevents retraction of the shield during assembly of the needle assembly on the pen injector.

The safety shield system of the present invention is preferably, but not exclusively, adapted for use with pen injectors. That is, although the safety shield system of the present invention is specifically designed for use with pen injectors of the type described herein, the inventive safety shield system may also be used with other devices including hypodermic syringes or other known or hereafter developed medicament delivery systems—the specific medicament delivery device not limiting the scope of spirit of the present invention. For ease of description, however, the inventive safety shield system will now be described for use with a pen injector. As set forth above, such pen injectors generally include a tubular body portion adapted to receive a conventional vial for dispensing a liquid medicament. The pen injector has an end configured to receive a pen needle such as, for example, the needle assembly of the present invention. Typically, the pen injector has an external thread to receive a complementarily configured thread on the needle assembly. Once the needle assembly is secured to the pen injector, the first end of the needle cannula pierces the rubber septum of the vial carried by the pen injector. Typical pen injectors may be single-dose, in which the entire contents of medicament within the vial are dispensed in a single injection, or multi-dose, in which only part of the contents of medicament within the vial are dispensed in an injection. For the latter case, the pen injector may include dose setting features.

In accordance with an embodiment of the present invention, the safety shield system includes a generally tubular clip member preferably having a tubular body portion received around the tubular hub portion of the hub assembly and a plurality of spaced laterally projecting resilient fingers. The free ends of the resilient fingers are hook-shaped opening toward the body portion of the pen injector. The safety shield system further includes a generally tubular reciprocable shield having a first tubular portion surrounding the clip member and a second tubular portion normally surrounding the second end of the needle cannula. As described below, a shield spring is provided that normally biases the shield to extend the second portion of the shield around the needle cannula. The shield may also include a plurality of spaced axially extending inwardly opening channel-shaped tracks on an inner surface of the shield which receive the resilient fingers of the clip member. During reciprocal motion of the shield as described below, the axially extending channel-shaped tracks guide the shield from a first position, wherein the shield second portion surrounds the second end of the needle cannula, to a second position, wherein the second end of the needle cannula is exposed for injection of a patient. The safety shield system further includes a spring resiliently biasing the shield axially to normally extend the shield second portion to surround the second end of the needle cannula. Thus, during use of the pen injector, the health care worker or patient presses the end of the shield against the area to be injected, which retracts the shield to the second position against the force of the spring. In a preferred embodiment, the shield is cup-shaped including the first and second tubular portions described above and has a generally closed end portion having a central opening which receives the second end of the needle cannula therethrough during injection. Following use, the spring automatically extends the shield to enclose the second end of the needle cannula.

The shield includes an opening spaced from but near the open end of the shield, and means is provided to prevent the free end of the resilient finger from being received in the opening during movement of the shield from the first position, in which the shield encloses the tip of the second or patient end of the needle cannula, to the second position, in which the tip of the second end of the needle cannula is exposed. Thus, the shield may be retracted to expose the tip of the second end of the needle cannula during injection, but the resilient finger will lock into the opening when the spring causes the shield to move from the second position to the third position, in which the shield lockingly encloses the tip of the second end of the needle cannula. The shield is thereby locked in place enclosing the tip and the second end of the needle cannula following injection. In one embodiment, wherein the free end of the resilient fingers are hook-shaped as described above, the hook-shaped portion of the finger is received through the opening and securely locks the shield in the closed position. In a preferred embodiment, each of the channel-shaped tracks include an opening which receives and secures each of the locking fingers. The improved safety shield system thus permits one-time retraction of the safety shield during injection and locks the safety shield to enclose the second end of the needle cannula following injection. Although various means may be utilized in accord with the invention to prevent receipt of the locking fingers in the openings during retraction of the safety shield to expose the needle cannula, one embodiment includes a resilient detent or finger portion in the tracks adjacent the opening which resiliently biases the fingers of the clip member inwardly, such that the resilient fingers of the clip member travel past the opening during retraction of the shield to the second position as described above. Further, the resilient detents catch the hook-shaped end portions of the resilient fingers during extension of the shield from the second position to the third position, assuring locking of the shield in the third or extended position following injection. In another embodiment, the hook-shaped portion of the finger is larger than the opening such that the finger slides over the opening when the shield is moved to the second position. The openings include a chamfer which catch the hook-shaped portions of the fingers when the shield is moved from the second position to the third position.

The safety shield system further includes a removable cup-shaped cap which is received over the shield prior to use. Prior to use, the cap is removed and the pen injector is ready for use as described above. However, the cap of the improved safety shield system of this invention may also be used to safely store and dispose of the needle assembly after use. As described herein, the second end of the needle cannula is protected following injection by the safety shield which is locked in the extended position surrounding the second end of the needle cannula. The needle cannula and safety shield system may then be safely stored in the cap for disposal by removing the needle cannula and needle assembly from the pen injector and inserting the first end of the needle cannula into the cup-shaped cap which is configured and adapted to lockingly receive the needle assembly for safe disposal. That is, the first end of the needle cannula is then located in the cup-shaped cap preventing exposure to the needle cannula and the second end portion is safely enclosed by the safety shield which is locked in the extended position protecting the second end of the needle cannula. Another embodiment of the subject invention includes a top cap and a bottom cap which interlock with each other to completely encompass the needle cannula.

The safety shield system in accordance with the present invention thus provides reliable operation and protection from the needle cannula after use of the needle assembly. In certain implementations, the generally tubular safety shield moves axially guided by the axially extending channel-shaped tracks as described herein, thereby eliminating rotational movement of the shield or a complex track system. The tubular body portion of the clip member includes a plurality of spaced axially extending radially projecting ribs which are received in axially extending grooves in the tubular portions of the shield, assuring axial movement of the shield during retraction and extension of the shield as described herein. The resilient fingers of the clip member include a U-shaped portion integrally connected to the tubular portion of the clip member and hook-shaped free end portions as described herein. This configuration provides additional resiliency for the hook-shaped end portions of the fingers. Further, the U-shaped portion of the fingers preferably open toward the generally closed end of the shield and the spring includes a first end received in the U-shaped portions of the fingers and a second end biased against the generally closed end of the shield assuring reliable movement of the shield.

The safety shield system of this invention also prevents retraction of the shield during assembly of the needle assembly on the pen injector. As set forth above, one problem with certain pen needles has been potential piercing of the cap during threaded assembly of the cap and shield assembly on the pen injector thereby exposing the user to puncture. The cap of the improved safety shield system includes a plurality of radially inwardly projecting ribs which are received in the axially extending grooves in the tubular portion of the shield against the axially projecting ribs on the clip member. The grooves in the tubular portion of the shield preferably extend through the sidewall of the shield from adjacent the generally closed end to the ribs. These internal ribs on the cap prevent retraction of the shield while the shield is held within the cap and during threaded assembly of the cap and shield assembly on the pen injector, thereby preventing accidental puncture during assembly.

The safety shield system in accord with aspects of this invention thus permits normal operation of the safety shield to retract the shield during injection and automatically extends and locks the shield following injection to prevent inadvertent contact with the second end of the needle cannula. Further, as described herein, the needle assembly may then be safely stored in the cup-shaped cap or cover for disposal wherein the first end of the needle cannula is located in the cup-shaped cover and the second end is protected by the safety shield. Other advantages and meritorious features of the safety shield system of this invention will be more fully understood from the following description of the embodiments, the appended claims and the drawings.

DETAILED DESCRIPTION OF THE PREFERRED EMBODIMENTS

Figure 1:
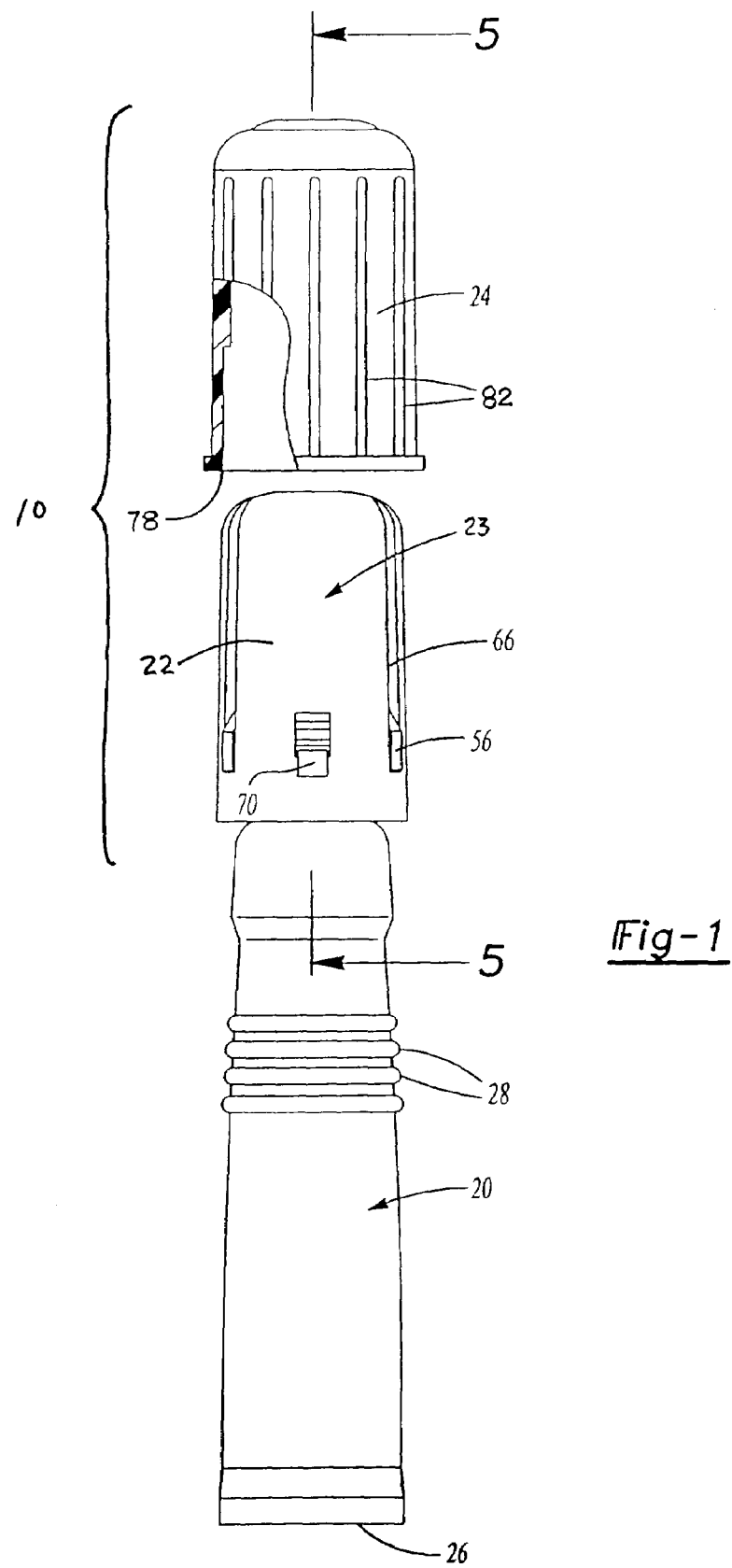
FIG. 1 is a side view of one embodiment of the safety shield system in accordance with the present invention with the cap removed.

As set forth above, the improved safety shield system is particularly but not exclusively adapted for use with a pen injector. As will be understood, however, the safety shield system of this invention may also be used with other injection devices, including, by way of illustration and not limitation, hypodermic syringes and other known or hereafter developed drug delivery devices.

The needle assembly 23 of the present invention may be removably provided on a pen injector 20. The pen injector depicted in FIG. 1 includes an open end 26 which may include external ribs 28 to facilitate gripping of the pen injector 20 by the user during attachment of the needle assembly 23 to the pen injector 20. As shown in FIG. 2, the pen injector 20 is sized and shaped to receive a vial 30 (shown in phantom) having a pierceable closure such as a rubber septum (not shown) in an open tubular end portion 31 of the vial.

Figure 2:
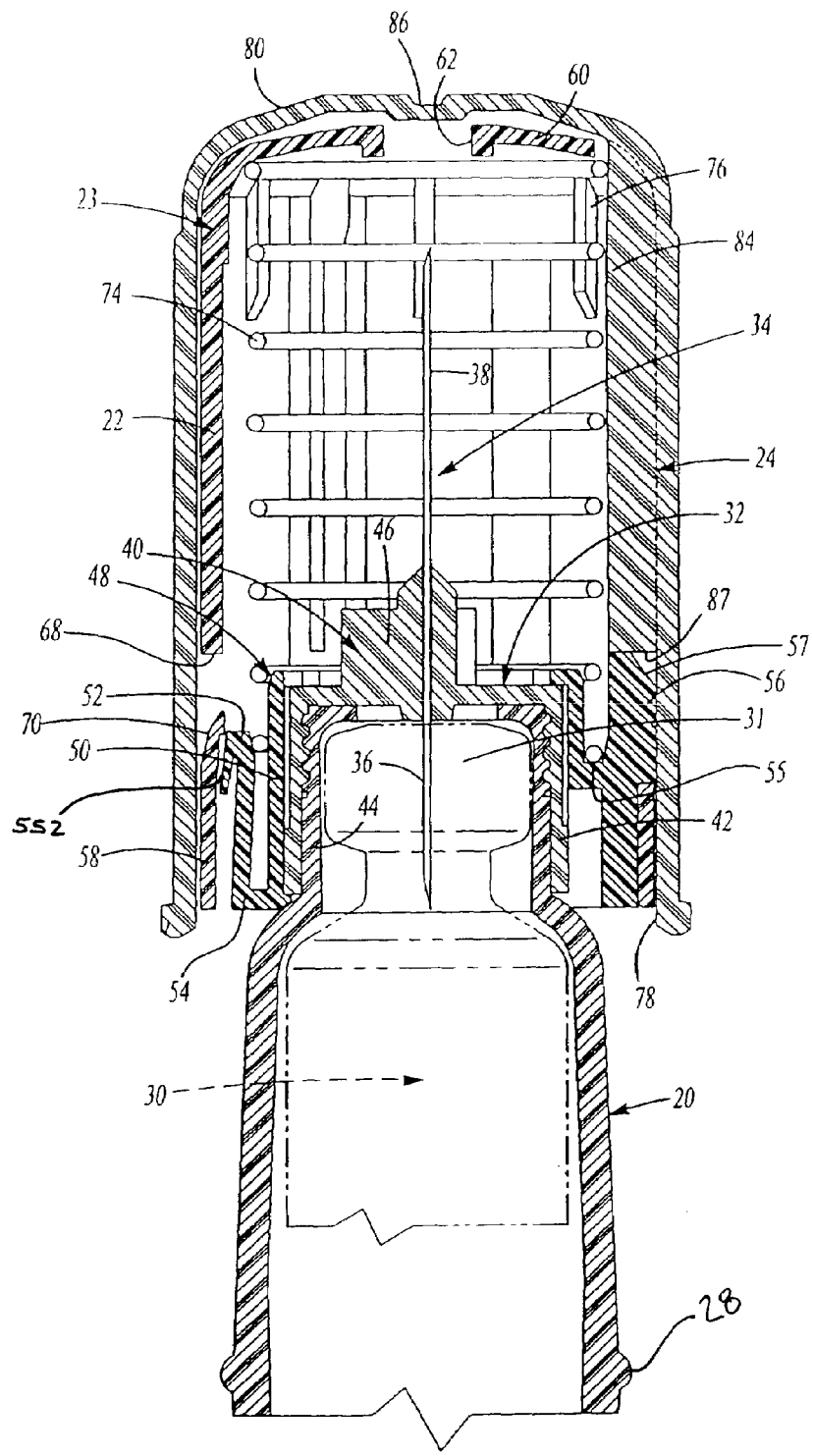
FIG. 2 is a partial cross-sectional view of the safety shield system of the present invention with the needle assembly in the cap.

With reference first to FIG. 1, the inventive safety shield system is there depicted and generally indicated by reference number 10. The safety shield system 10 comprises a needle assembly 23 and cap 24, each of which are discussed in detail below. The needle assembly 23 comprises a safety shield 22, a hub assembly 22 and a coil spring 74.

Figure 3:
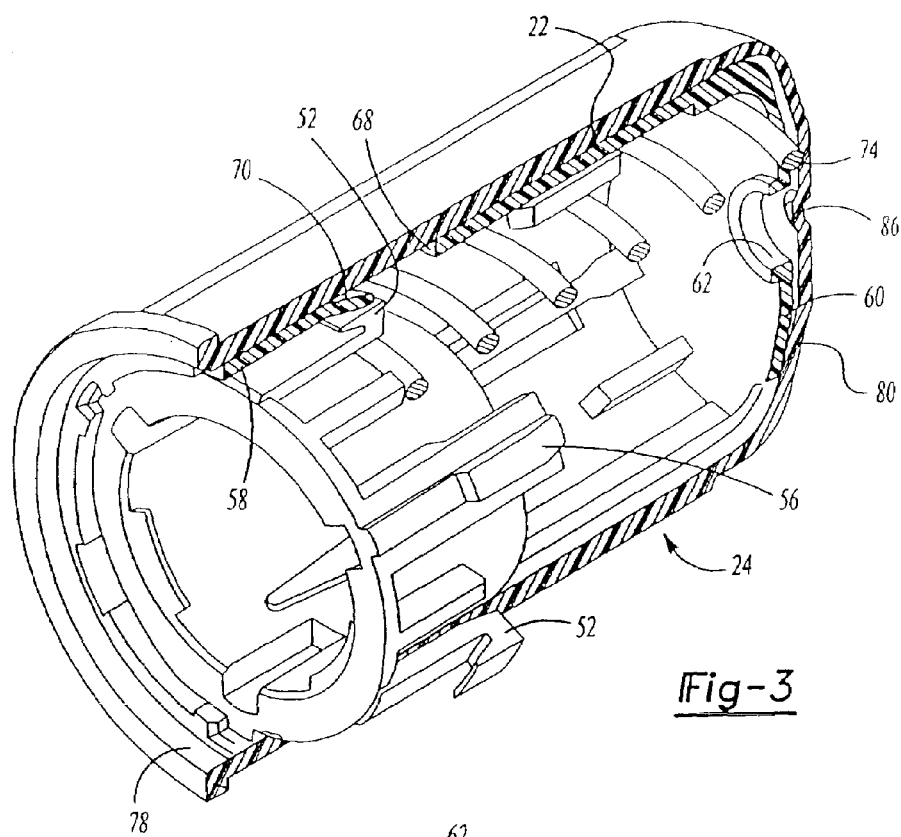
FIG. 3 is a partial cross-sectional elevational view of the safety shield system of the present invention.
Figure 4:
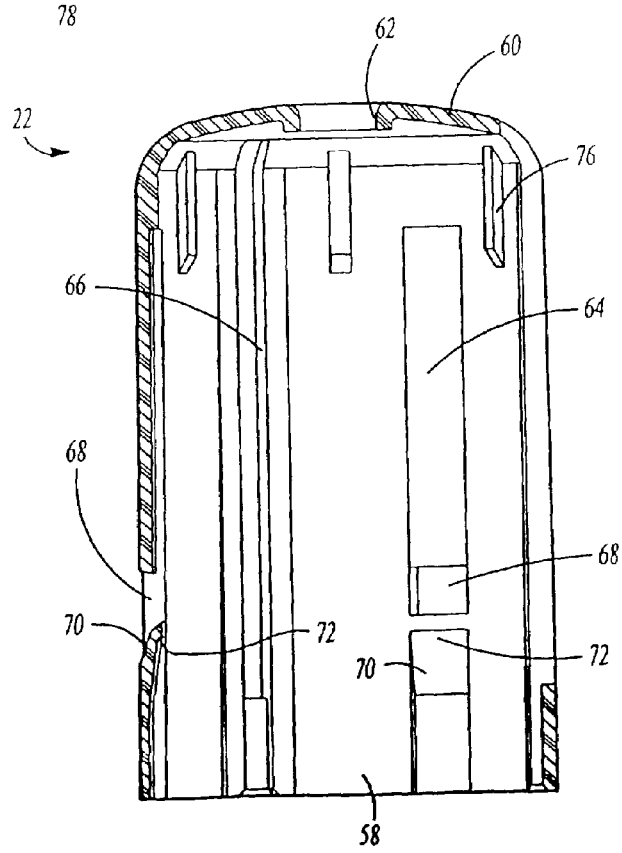
FIG. 4 is a cross-sectional view of the safety shield of the present invention.

The needle assembly 23 of the present invention will now be discussed in detail. Referring first to FIGS. 2-4, the safety shield 22 is generally tubular having an open end 58 and preferably including a generally closed end 60 having an axial opening 62 therethrough which receives the second end 38 of a needle cannula 34 supported by the hub assembly 32, as described below. The second end 38 of the cannula 34 is intended to pierce the skin of a patient during use of the pen injector 20 to inject a medicament into the body of a patient. The cannula 34 also includes a first end 36 for piercing the pierceable closure of the vial 30 when the needle assembly 23 is provided on the pen injector 20. The shield 22 further includes a plurality of circumferentially spaced longitudinally or axially extending channel-shaped tracks 64 in an internal surface of the tubular portion of the shield 22 that receives hook-shaped fingers 52 (discussed below) and a plurality of circumferentially spaced axially extending slots or grooves 66 which receive radial ribs 56 on clip member 48 (both discussed below). The longitudinal axis of the safety shield 22 is coincident with the needle cannula 34. In one embodiment, the axial channel-shaped tracks 64 each include a radial opening 68 which is generally adjacent to but spaced from the open end 58 of the shield 22 in certain implementations of the invention. Each of the axial channel-shaped tracks 64 may include an inwardly projecting resilient integral tang or finger portion 70 adjacent the opening 68 closest to the open end 58 as seen in FIG. 4. The resilient tangs or finger portions 70 resiliently bias the hook-shaped fingers 52 inwardly and preferably include a ledge 72 releasably retaining the shield 22 in the extended position prior to injection as shown in FIG. 2 and further described below.

A coil spring 74 is biased between the clip member 48 and the generally closed end 60 of the shield 22, resiliently urging the shield 22 toward the extended position to enclose the second end 38 of the needle cannula 34, as shown in FIG. 2. The inside surface of the shield 22 includes a plurality of circumferentially spaced radially projecting ribs 76 that center the coil spring 74 in the shield 22. The cup-shaped cap 24 includes a closed end 80 and an open end 78. The open end receives the needle assembly 23 and needle cannula and hub assembly 32. In one embodiment, the internal surface of the cap 24 includes a plurality of radially projecting ribs 84 that extend axially from adjacent the closed end 80 to the ends of the radial ribs 56 and which prevent retraction of the safety shield 22 during assembly on the pen injector 20. The external surface of the cap 24 may also include ribs 82 to assist in gripping the cap 24 during assembly of the needle assembly 23 on the pen injector 20. The closed end 80 of the cap 24 also includes an inwardly projecting dimple 86 which is received in the opening 62 of the shield 22 centering the cap 24 on the shield 22. Other details of the embodiments of the needle assembly 23 will be discussed below in the description of the assembly and operation of the disclosed embodiments of the present invention.

The hub assembly 32 carries the needle cannula 34 which extends through a hub member 40 to define a first end 36 that extends into the pen injector 20 to pierce the closure of the vial 30 or other container and the second opposed end 38 used for injection. The hub member 40 includes a tubular rim portion 42 that is preferably threadably received on a tubular end portion 44 of the pen injector 20 and a central portion 46 that receives and secures the needle cannula 34. The needle cannula 34 includes a lumen or small passage therethrough for transferring fluid in the vial 30 to the user for self-injection or administration by a health care worker. The tubular rim portion 42 of the hub member 40 may include internal threads for threaded receipt of the hub member 40 on the externally threaded end portion 44 of the pen injector 20.

The safety shield system 10 includes a generally tubular clip member 48 having a tubular body portion 50 which is received around the tubular rim portion 42 of the hub member 40, as shown in FIG. 2. The clip member 48 has a plurality of laterally projecting resilient hook-shaped fingers 52. The clip member 48 may be formed of a resilient polymeric material, such as polypropylene, such that the fingers 52 are able to flex inwardly and resiliently flex outwardly as described below. Alternatively, the clip member 48 may be formed of a metal stamping or may be integrally formed with hub member 40. As shown in FIG. 2, for example, the fingers 52 are supported on a U-shaped portion 54 which further improves the resiliency of the fingers 52 as they flex inwardly and outwardly. The clip member 48 further includes a plurality of circumferentially spaced radially extending ribs 56 which prevent rotational movement of the shield 22 and guide the shield 22 during axial movement of the shield 22 as described below.

The operation of one embodiment of the safety shield system 10 of the present invention will now be described. An important advantage of the needle assembly 23 of the present invention is that it may be preassembled with the needle cannula 34 and hub assembly 32 and supplied to the patient or end user as an assembly ready for use. The first step taken by the patient or end user is to remove the needle assembly 23 from its container, which includes the cap 24 and a bottom cap 193 (see FIG. 9). Preferably, only the bottom cap 193 is removed, as depicted in FIG. 2. As noted herein, the cap 24 is provides a locking seal over the first end 36 of the needle cannula 34 after use. The needle assembly 23 is then attached to the pen injector 20 by threading the tubular rim portion 42 of the needle cannula and hub assembly 32 onto the tubular end portion 44 of the pen injector 20. As can be seen from FIG. 2, the internal ribs 84 on the cap 24 are aligned with the ribs 56 of the clip member 48 and prevent inadvertent movement of the safety shield 22 during assembly of the needle assembly 23 and pen injector 20. Such inadvertent movement could drive the second end 38 of the needle cannula 34 through the opening 62 of the shield 22 and puncture the cap 24, thereby exposing the end user to the tip of the second end 38 of the needle cannula 34. The vial 30 may be previously loaded into the pen injector 20 and the open end 26 of the pen injector 20 may be closed by an end cap (not shown). The threaded assembly of the needle assembly 23 and pen injector 20 causes the first end 36 of the needle cannula 34 to pierce the closure of the vial 30 as the tubular rim portion 42 of the hub member 40 is threaded onto the rim portion 44 of the pen injector 20. Alternatively, the vial 30 may be inserted into the pen injector 20 following assembly of the needle assembly 23 and pen injector 20.

Figure 5:
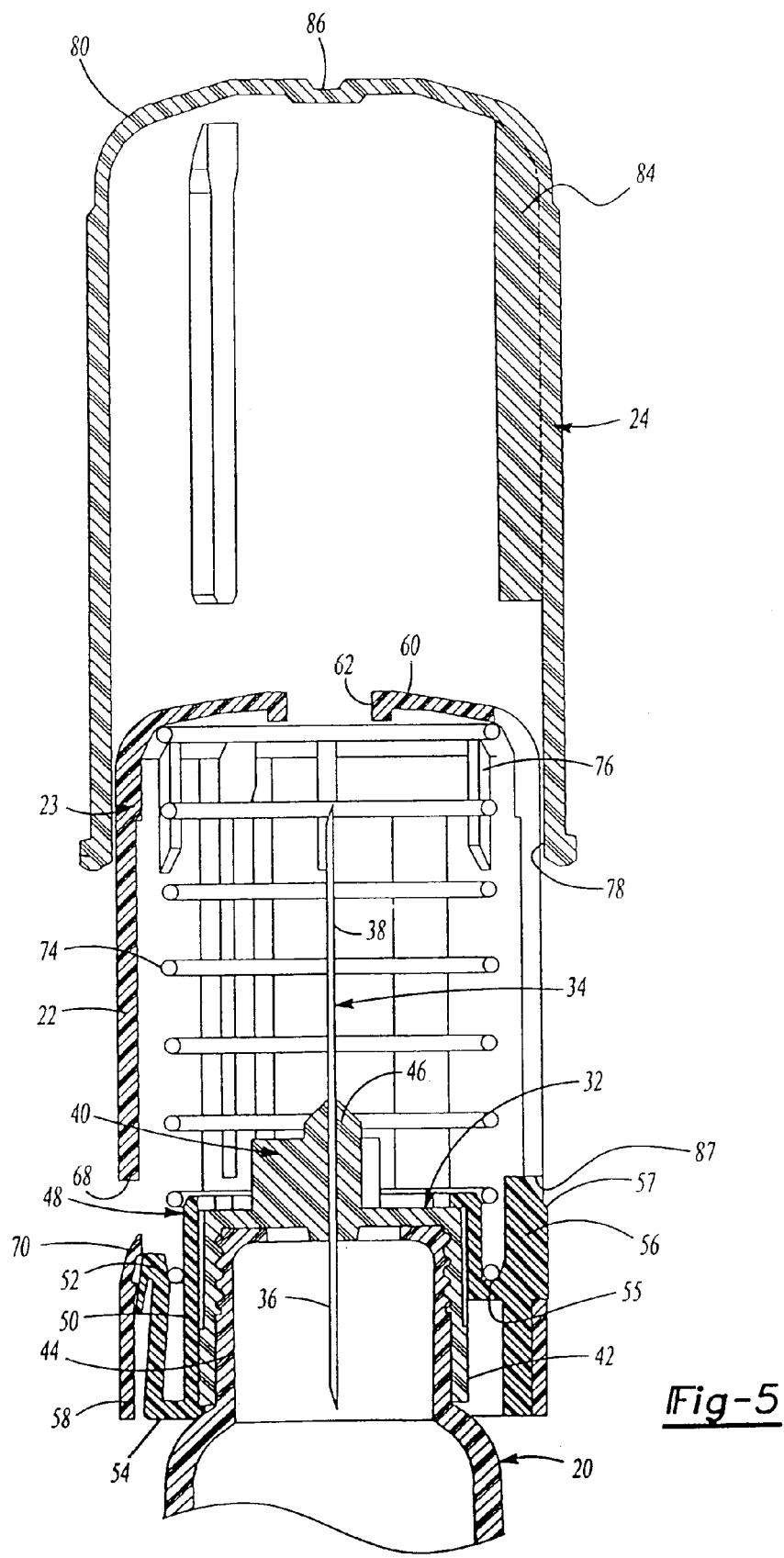
FIG. 5 is a side cross-sectional view taken along line 5-5 of FIG. 1.

Once the needle assembly 23 and pen injector 20 are assembled together, the cap 24 is removed as shown in FIGS. 1 and 5. The needle assembly 23 of the present invention is then ready for use.

Figure 6:
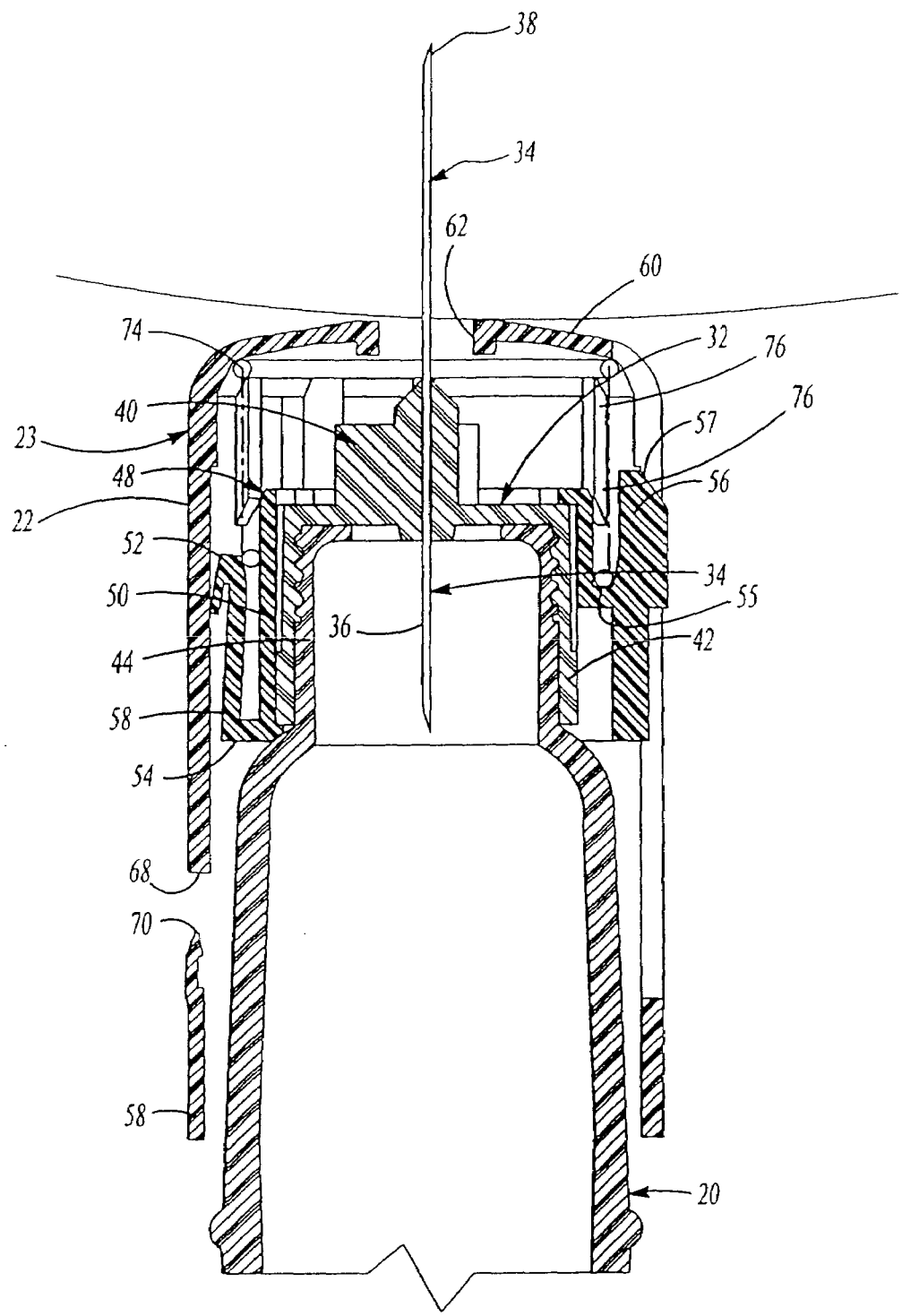
FIG. 6 is a cross-sectional view of the needle assembly of the inventive safety shield system during use.
Figure 14:
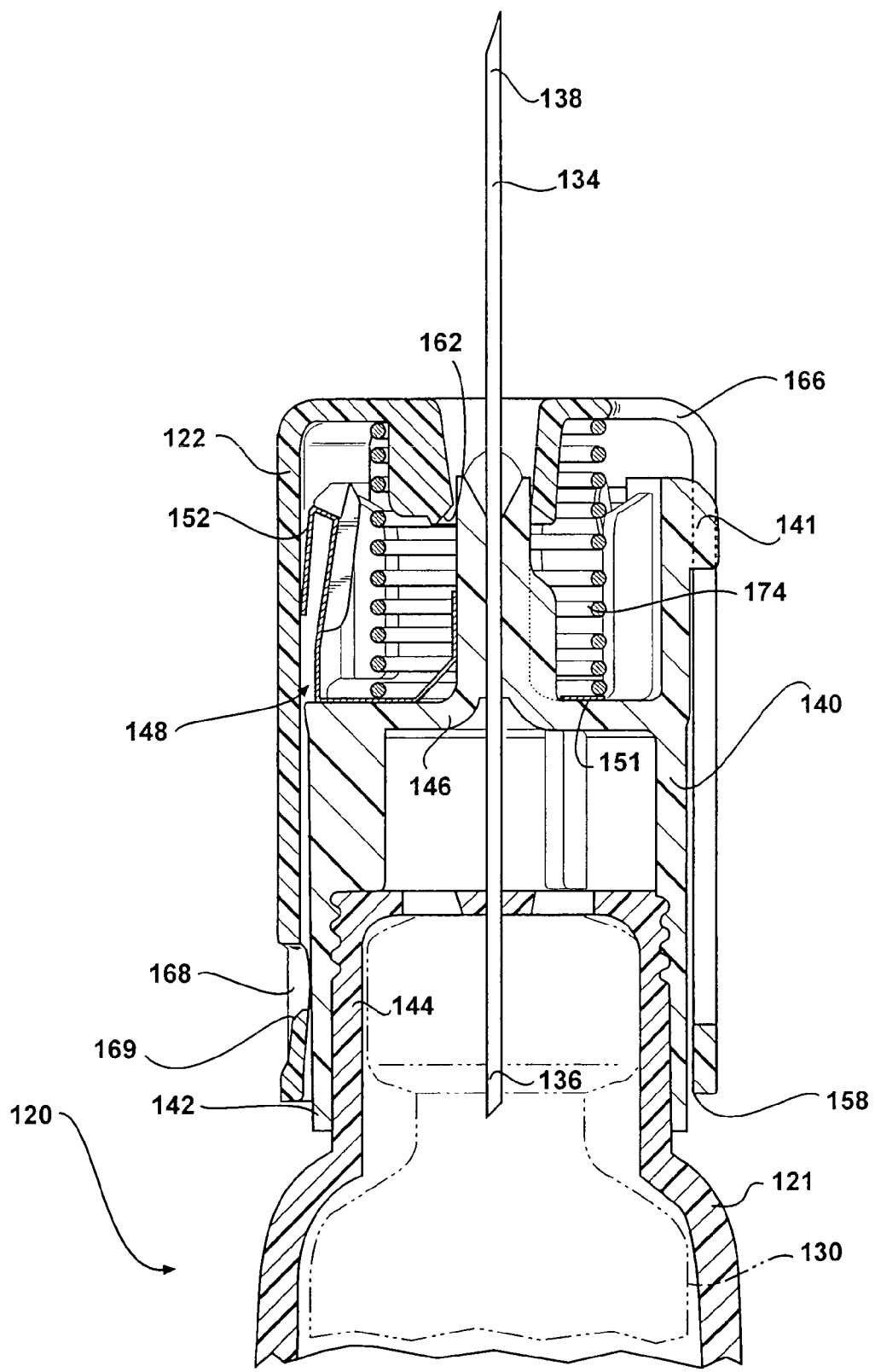
FIG. 14 is a cross-sectional view of the safety shield system of FIG. 9 during injection of a medicament.

As set forth above, the needle assembly 23 is particularly, but not exclusively, suitable for pen needle injectors typically used for self-administration of a liquid medicament. During use, the patient simply depresses the generally closed end 60 of the safety shield 22 against the body area to be injected, as shown in FIG. 6. As shown in FIGS. 2 and 5, the hook-shaped fingers 52 are releasably retained by the inwardly projecting tangs or finger portions 70 of the shield 22 preventing inadvertent retraction of the shield 22 and providing some resistance to movement of the shield 22 during injection which is considered an advantageous feature of this invention. Further, the fingers 52 are resiliently biased inwardly by the shield 22, such that retraction of the shield 22 when the generally closed end 60 of the shield 22 is pressed against the skin causes the fingers 52 to move over the openings 68 and move into the channel-shaped tracks 64 during initial retraction of the shield 22, exposing the second end 38 of the needle cannula 34 which is received through the opening 62 of the shield 22, resulting in injection of the patient. The tip 552 of the fingers may be longer than the opening in the axial direction. Consequently, during actuation of the shield 22 (as seen in FIGS. 6 and 14), the top portion of the finger has passed the opening 68 before the end of the tip 552 moves into the opening. As such, the top 552 of the finger does not contact the top of the opening 68 during such actuation. Rotation of the shield 22 relative to the needle cannula and hub assembly 32 is prevented by the ribs 56 which follow the axial slots or grooves 66 assuring axial movement of the shield 22.

Figure 7:
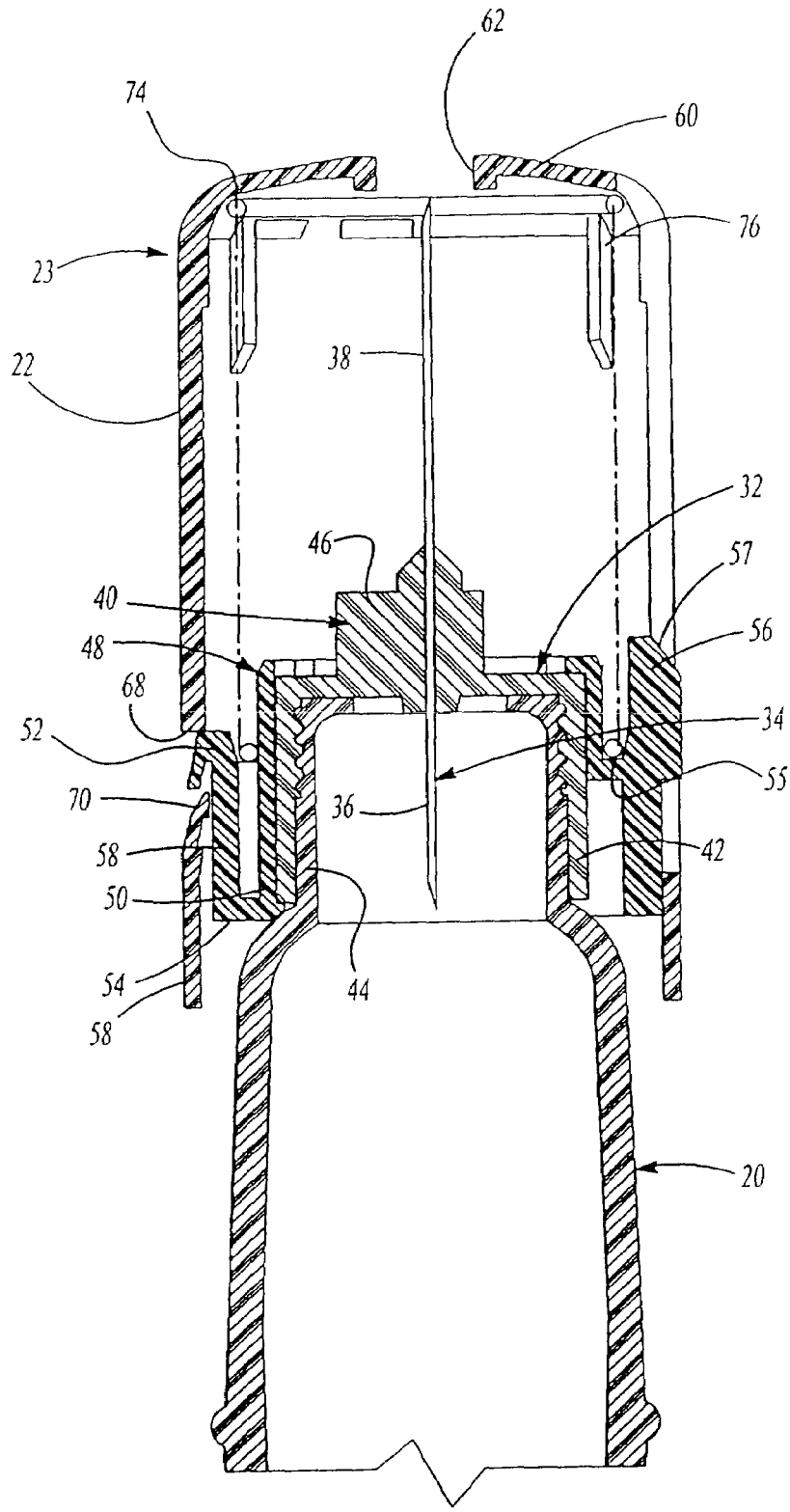
FIG. 7 is a cross-sectional view of the needle assembly of the inventive safety shield system after use with the safety shield lockingly enclosing the second end of the needle cannula.

Following injection, the needle cannula 34 is withdrawn from the patient and the shield 22 is simultaneously extended by the coil spring 74, such that the second end 38 of the needle cannula 34 is never exposed. The shield 22 is extended axially as the needle cannula 34 is withdrawn because the hook-shaped fingers 52 move in the axial channel-shaped track 64 and the radial ribs 56 move through the slots or grooves 66. Upon full extension of the shield 22 to enclose the second end 38 of the needle cannula 34, the hook-shaped fingers 52 are received through the openings 68 and, in certain implementations of the invention, the hook-shaped portion is received around the inwardly projecting tang 70, locking the shield 22 in the extended position as shown in FIG. 7. The shield 22 cannot be moved from the position shown in FIG. 7 following injection to re-expose the second end 38 of the needle cannula 34.

Figure 8:
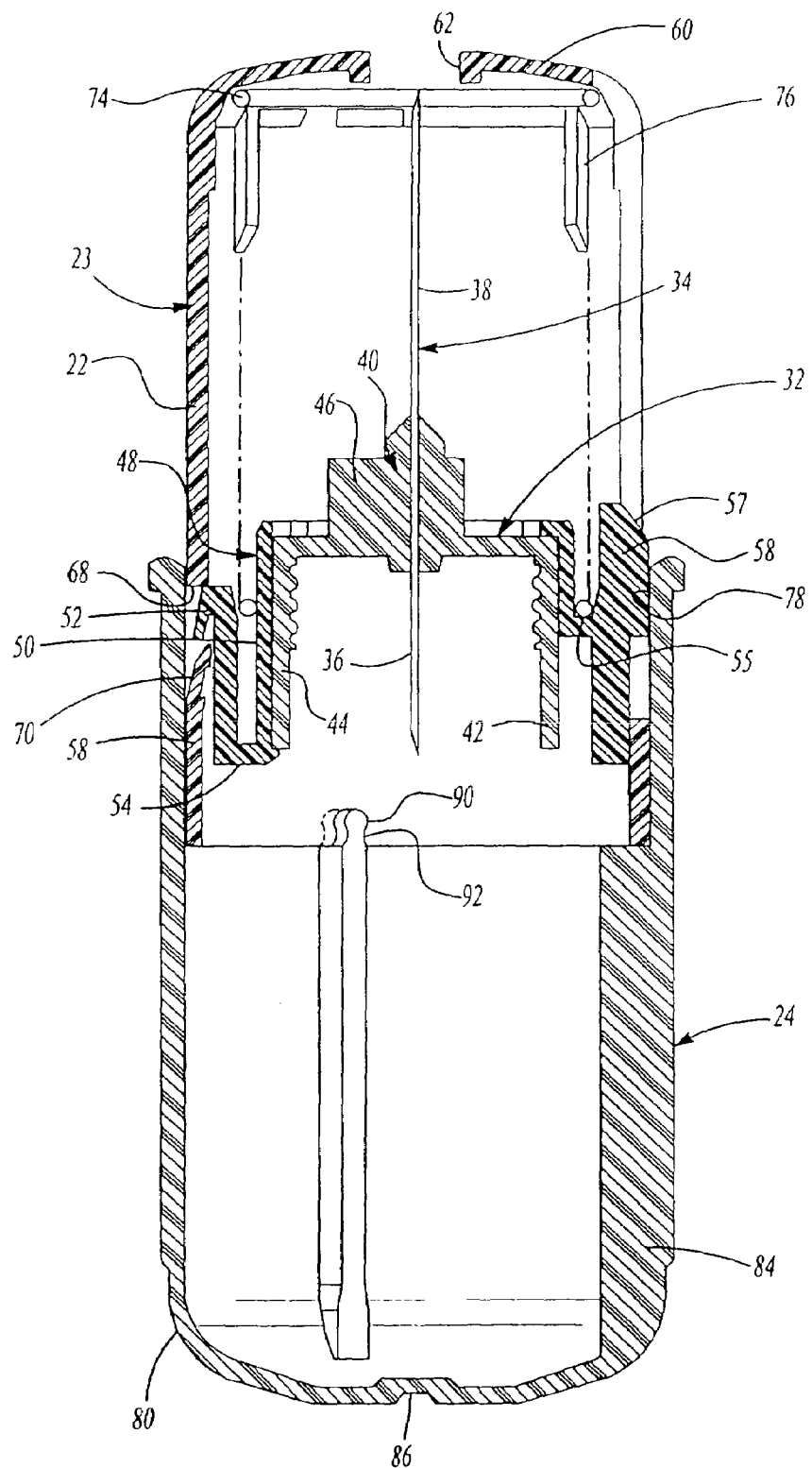
FIG. 8 is a cross-sectional view of the needle assembly of the inventive safety shield system after use with the cap enclosing the first end of the needle cannula.

After use, the needle assembly 23 may be removed from the pen injector 20 by unthreading the tubular rim portion 42 of the hub member 40 from the threaded tubular end portion 44 of the pen injector 20. The needle assembly 23 may then be inserted into the cap 24, as shown in FIG. 8 to lockingly cover the first end 36 of the needle cannula 34. The first sharp end 36 of the needle cannula 34 is thus safely received in the cap 24 and the second end 38 of the needle cannula is protected by the safety shield 22, which is locked in the extended position, providing for safe disposal of the entire needle assembly 23. The internal ribs 84 of the cap 24 may be designed to provide an interference fit with the needle assembly 23, thereby preventing inadvertent removal of the assembly from the cap 24 and inadvertent exposure to either end of the needle cannula 34 following disposal. As shown in FIG. 8, one or more of the ribs 84 may include a ball-shaped end portion 90 which is received in a socket 92, securing the assembly in the cap 24.

The safety shield system 10 of the present invention thus provides several important advantages over the prior art systems. First, the needle assembly 23 and cap 24 may be easily attached to the pen injector 20 without inadvertent retraction of the needle assembly 23 on the pen injector 20 and piercing of the cap 24, exposing the needle cannula 34 to the patient. This safety feature is provided by the radial ribs 56 on the hub member 40, which engage the internal ribs 84 of the cap 24 preventing retraction of the shield 22 during assembly. Upon removal of the cap 24, the pen injector 20 may be easily utilized for self-injection by the patient by depressing the generally closed end 60 of the safety shield 22 against the area to be injected without ever exposing the second end 38 of the needle cannula 34 to view. Following injection, the safety shield 22 is automatically extended by the spring 74 to enclose the second end 38 of the needle cannula 34 and locked in the extended position by the resilient fingers 52 which extend into the openings 68 through the channel-shaped tracks 64. The hook-shaped fingers 52 also lock over the resilient integral tangs 70. Following use, the needle assembly 23 may be easily removed from the pen injector 20 by unthreading the tubular rim portion 42 of the hub member 40 from the tubular end portion 44 of the pen injector 20, reversing the assembly. The first end 36 of the needle cannula 34 may be covered to prevent accidental needle stick injury to the use by inserting the needle assembly 23 into the cap 24 (see, e.g., FIG. 8), providing for safe disposal of the needle assembly 23 wherein both ends of the double ended needle cannula 34 are safely enclosed.

As set forth above, the needle cannula and hub assembly 32 is assembled in the needle assembly 23 prior to receipt by the end user, wherein the hook-shaped fingers 52 are releasably retained by the ledge 72 of the inwardly projecting tangs 70 during assembly of the shield 22 on the clip member 48. The cap 24 is assembled on the shield 22 by disposing the inwardly projecting ribs 84 of the cap 24 into the slots 66 in the shield 22 as best shown in FIG. 2, wherein the end portions 87 of ribs 84 engage the ends of the radial rib portions 56. The radial ribs 56 in this embodiment include a chamfered end 57 which guides the ribs 56 into the slot 66 and the radial ribs 56 are connected to the tubular body portion by web portions 55. Further, the coil spring 74 is received between the radial ribs and the tubular body portion 50 against the web portion 55 as shown in FIG. 2. The radial ribs 56 may thus be resiliently flexed inwardly during assembly. As set forth above, the clip member 48 may be formed of a resilient polymeric material, such as polypropylene or formed of a metal stamping. Other components of the needle assembly 23 and the cap 24 are preferably formed of a sterilizable material including a polymeric material which can be injection molded. Thus, a suitable material for various parts of the needle assembly 23 is a sterilizable polypropylene.

Having described one embodiment of the safety shield system 10 of the present invention, it will be understood that various modifications may be made to the disclosed embodiment within the purview of the appended claims. For example, other locking means for locking the shield 22 in the extended position following injection may be utilized. Further, locking means may be provided within the cap 24 for locking the needle assembly 23 within the cap 24 following removal of the needle assembly 23 from the pen injector 20 and storage of the assembly in the safety cap 24 as shown in FIG. 8, including interlocking ribs, etc. Further, certain improved features of the safety shield system 10 of this invention may be utilized with conventional pen needle and shield assemblies, including, for example, the radial ribs 84 on the internal surface of the cap 24 which prevent depression or retraction of the shield 22 during assembly of the safety shield 22 and cap 24 on the pen injector 20 as described above.

Figure 9:
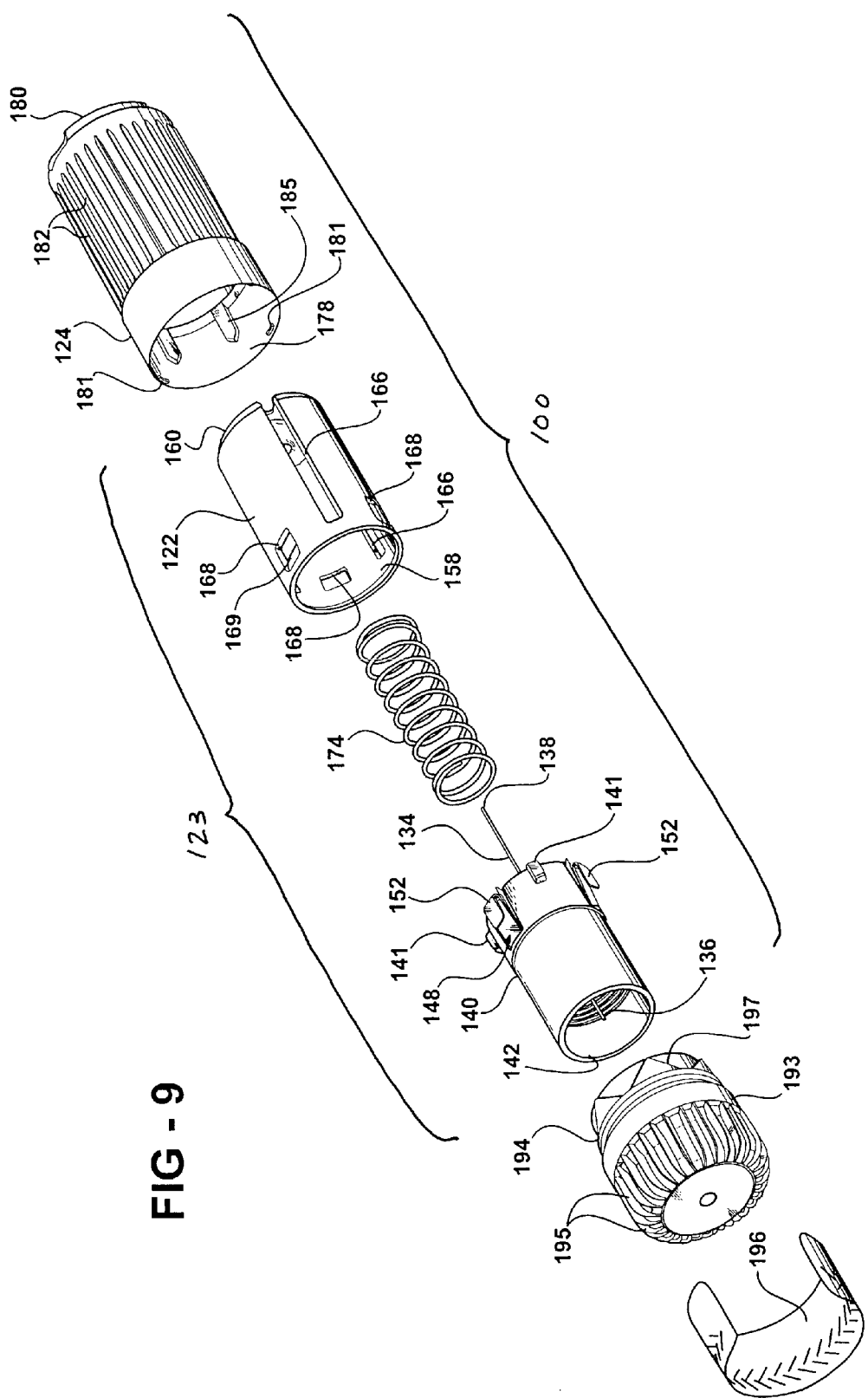
FIG. 9 is an exploded perspective view of another embodiment of the safety shield system of the present invention.
Figure 10:
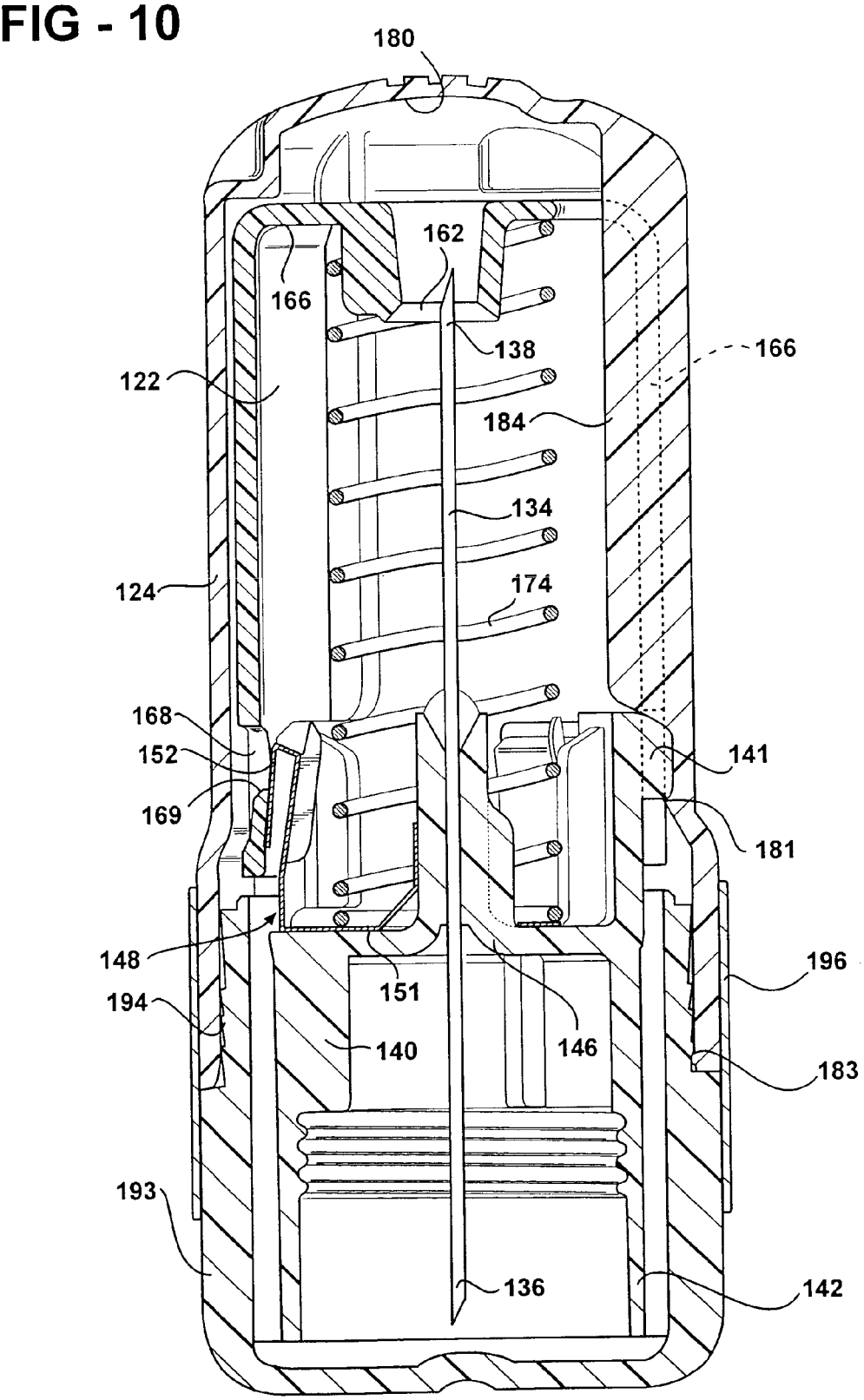
FIG. 10 is a cross-sectional view of the safety shield system of FIG. 9.
Figure 11:
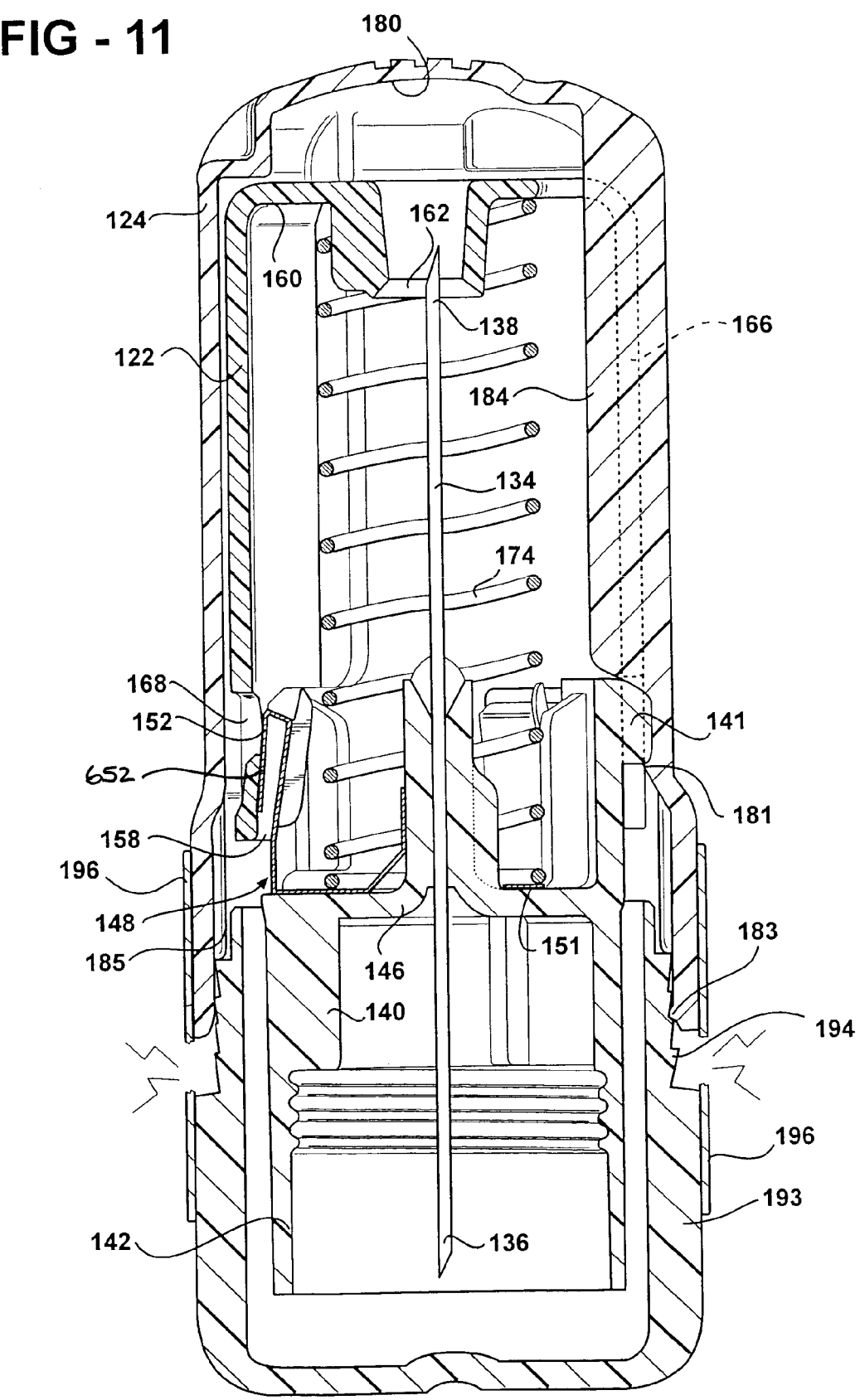
FIG. 11 is a cross-sectional view of the safety shield system of FIG. 9 illustrating a bottom cap being partially detached from a top cap.

Referring now to FIGS. 9-15, another embodiment of the safety shield system 100 of the present invention is shown. In those Figures, and in the accompanying description thereof, like numerals increased by one hundred indicate like or corresponding parts throughout the several views. FIGS. 9-11 illustrate the safety shield system 100 and FIGS. 12-15 illustrate the safety shield system 100 on a pen injector 120. As shown in FIGS. 12-15, the pen injector 120 includes a body portion 121 for receiving a container 130, such as a vial 130 containing a liquid medicament.

As with the previously described embodiment, the inventive safety shield system 100 depicted in FIGS. 9-15 comprises a needle assembly 123 and cap 124, each of which is described in detail below.

The safety shield system 100 includes a hub member 140 removably mountable to the body portion 121. The hub member 140 includes a tubular rim portion 142 which is preferably threadably received on a tubular end portion 144 of the pen injector 120. The hub member 140 also includes at least one radially extending rib 141 and a central portion 146 which receives and secures a needle cannula 134. In particular, the needle cannula 134 is mounted to and extends through the hub member 140. Specifically, the needle cannula 134 has a first end 136 extending into the body portion 121 for fluid communication with the container 130 and a second end 138 extending away from the body portion 121 for injection and transfer of the liquid medicament from the container 130 to a user. As discussed above, the needle cannula 134 includes a lumen or small passage therethrough for transferring liquid medicament in the vial 130 to the user for self-injection or administration by a health care worker.

Referring to FIGS. 9-11, the safety shield 122 system includes a clip member 148 mounted to the hub member 140 and having at least one laterally projecting resilient finger 152. Preferably, the clip member 148 includes a plurality of spaced laterally projecting resilient fingers 152. Each of the resilient fingers 152 include a hook-shaped end portion. The clip member 148 may be formed of a metallic material and includes a common base 151 with each of the resilient fingers 152 extending from the base 151. The base 151 is in turn fastened to the central portion 146 of the hub member 140. Alternatively, the clip member may be formed of other materials or integrally formed with the hub. The fingers 152 are able to flex inwardly and resiliently flex outwardly as described below.

Figure 15:
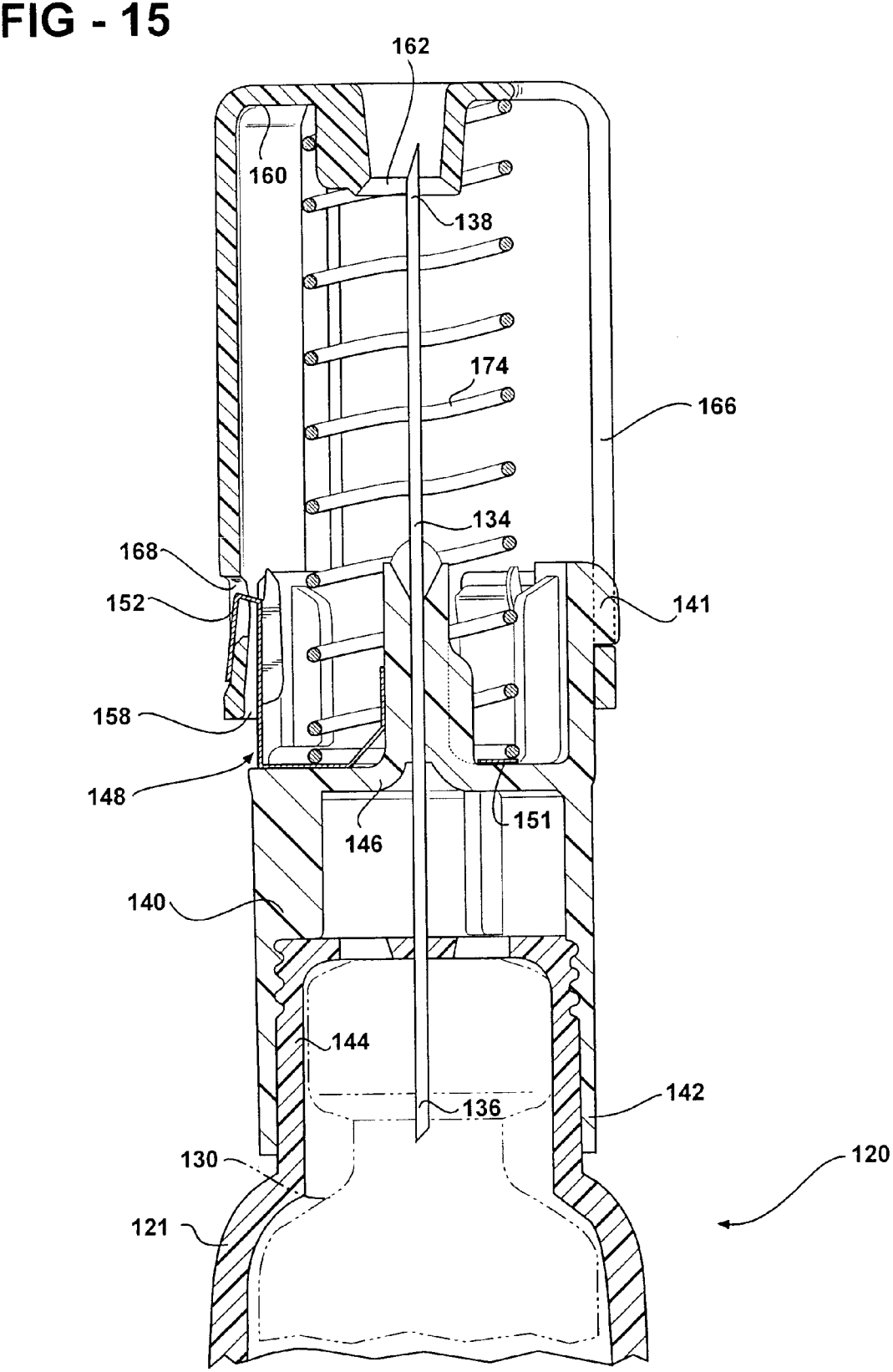
FIG. 15 is a cross-sectional view of the safety shield system of FIG. 9 following injection and with the safety shield lockingly enclosing the second end of the needle cannula.

A shield 122 is moveably mounted to the clip member 148 from a first position surrounding the second end 138 of the needle cannula 134, see FIGS. 10-13, and 15, to a second position exposing the second end 138 of the needle cannula 134, see FIG. 14, and finally to a third position, lockingly surrounding the second end 138 of the needle cannula 134, see FIG. 15. The shield 122 is generally cup-shaped having an open end 158 received around the clip member 148 and a generally closed end 160 having a central opening 162 therethrough receiving the second end 138 of the needle cannula 134 as described below. The shield 122 includes at least one opening 168 and preferably a plurality of openings 168 for receiving the fingers 152. The openings 168 extends through a side wall of the shield 122 for receiving the hook-shaped end portions of the fingers 152 therethrough to lock the shield 122 in the third position surrounding the needle cannula 134 (shown in FIG. 15). Each of the hook-shaped end portions of the fingers 152 preferably open toward the shield 122 for easy insertion into the openings 168. In particular, the shield 122 is first retracted to the second position to expose the needle cannula 134, see FIG. 14, and then extended to the third position surrounding the needle cannula 134 where the fingers 152 now lock the shield 122 in the first position to prevent further exposure of the needle cannula 134, see FIG. 15. It will be noted that the first and third positions do not differ with regard to the axial position of the needle shield 122 with regard to the needle cannula 134. These positions differ in that the needle shield 122 is movable out of the first position, and is not movable out of the third position.

In this embodiment of the subject invention, each of the hook-shaped end portions of the fingers 152 are larger than the corresponding openings 168 in the shield 122 such that the resilient fingers 152 initially slide over the openings 168 when the shield 122 is retracted to the second position. In particular, the end portions of the fingers 152 are longer than the openings 168 in the shield 122. The openings 168 each include a chamfer 169 with the fingers 152 first engaging the chamfer 169 and then extending into the openings 168 when the shield 122 returns to the first position from the second position.

Figure 13:
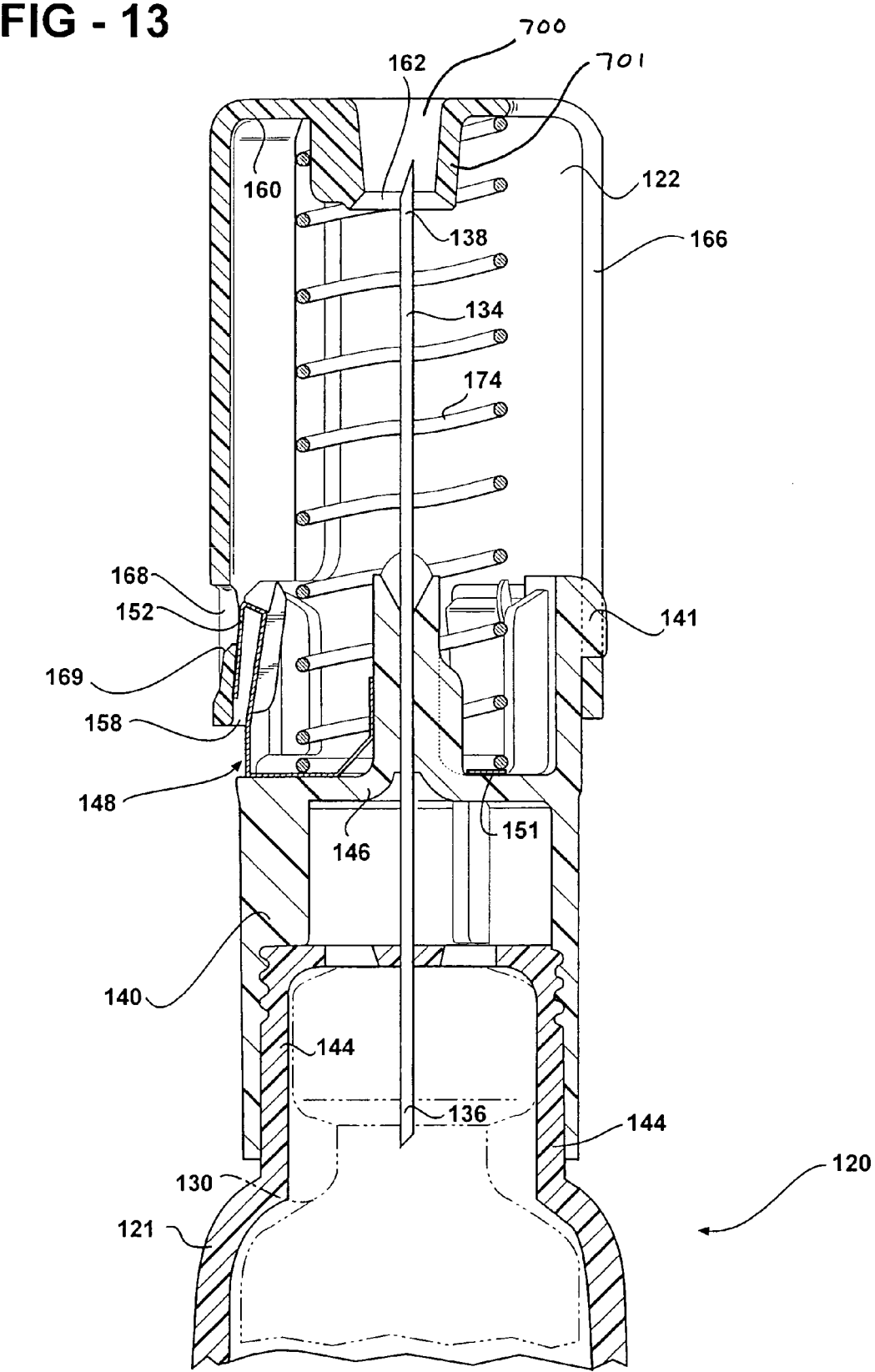
FIG. 13 is a cross-sectional view of the safety shield system of FIG. 9 mounted to the pen injector and having the top cap removed from the needle assembly.

As seen in FIG. 13, the second end of the needle cannula 138 is disposed within a channel 700 formed by a guide 701. As a result, the needle cannula is disposed within the opening 162, whether the tip of the needle is exposed or not. As the shield is retracted, the guide 701 prevents the needle tip from catching on the portions of the shield 122 adjacent to the opening 162.

The shield 122 further includes at least one radial groove 166 with the radially extending rib 141 of the hub member 140 being disposed within the groove 166 to prevent rotation of the shield 122 relative to the clip member 148. In the preferred embodiment, the shield 122 includes a plurality of spaced radial grooves 166 and the hub member 140 includes a plurality of spaced radially extending ribs 141 with a corresponding rib 141 disposed within each groove 166 to prevent rotation of the shield 122 relative to the clip member 148.

The needle assembly 123 further includes a spring 174 disposed within the shield 122 for continuously biasing the shield 122 toward the first and third position. Preferably, the spring 174 is a spiral spring having one end abutting the common base 151 and an opposed end biased against the generally closed end 160 of the shield 122.

As shown in FIGS. 9-12, a removable cup-shaped top cap 124 is also provided in this embodiment for initially being received over the shield 122. The top cap 124 includes an open end 178 which receives the hub member 140 as described below and a closed end 180. An internal surface of the cup-shaped top cap 124 includes inwardly projecting ribs 184 which are disposed within the grooves 166 of the shield 122. The ribs are designed to align with ribs 141 of the hub member 140 to prevent actuation during assembly. The shield 122 cannot be accessed when the top cap 124 is installed such that the shield 122 cannot retract relative to the hub member 140 when the top cap 124 is received over the shield 122. An external surface of the top cap 124 may also include ribs 182 to assist in gripping the top cap 124 during assembly of the shield system on the pen injector 120. The top cap 124 also includes first 181 and second 183 internal tabs. The first internal tabs 181 form an undercut which engages the ribs 141 of the hub member 140 to secure the top cap 124 to the hub member 140 and provide a degree of resistance during removal of the top cap 124 from the hub member 140. The top cap 124 further includes a first camming surface 185, the purpose of which will be discussed in detail below.

As shown in FIGS. 9-11, a removable cup-shaped bottom cap 193 is provided for this embodiment wherein the bottom cap 193 is likewise initially received over the hub member 140 opposite the top cap 124. The bottom cap 193 preferably interengages the top cap 124 when the top cap 124 is received over the shield 122 and the bottom cap 193 is received over the hub member 140 to completely surround the needle cannula 134. The interengagement between the top cap 124 and the bottom cap 193 forms a sterile barrier. The second internal tab 183 of the top cap 124 engages an annular notch 194 in the bottom cap 193 to secure the bottom cap 193 to the top cap 124 and provide a degree of resistance during removal of the bottom cap 193 from the top cap 124. The bottom cap 193 also includes a plurality of external ribs 195 for allowing a user to easily grip the bottom cap 193. Further, a frangible label 196 is at least partially adhered over both the top 124 and bottom 193 caps at the interface of the top 124 and bottom 193 caps. The frangible label 196 assists a user in identifying whether the bottom cap 193 has been separated from the top cap 124.

As with the top cap 124, the bottom cap 193 includes a second camming surface 197, best shown in FIG. 9. The first 185 and second 197 camming surfaces abut each other during rotation of the bottom cap 193 relative to the top cap 124 such that the bottom cap 193 simultaneously moves axially away from the top cap 124 during this rotation. In the embodiment shown, the first camming surface 185 is a plurality of inwardly facing ridges extending from the internal surface of the top cap 124 and the second camming surface 197 is a plurality of angled notches. During operation, the ridges abut the notches when the bottom cap 193 is interengaged with the top cap 124 such that during rotation of the bottom cap 193 relative to the top cap 124 the ridges ride along the angled notches to simultaneously move the bottom cap 193 axially away from the top cap 124.

The operation of this alternative embodiment of the safety shield system 100 will now be described in greater detail. As with the embodiment of FIGS. 1-8, one important advantage of the safety shield system 100 is that the needle assembly 123 may be preassembled and supplied to the patient or end user as an assembly ready for use.

The first step by the patient or end user is to break the frangible label 196 by rotating the bottom cap 193 relative to the top cap 124, see FIG. 11. As mentioned above, the bottom cap 193 includes the second camming surface 197 which engages the first camming surface 185 on the top cap 124. The bottom cap 193 therefore axially separates from the top cap 124 as the bottom cap 193 is rotated thereby exposing the tabular rim portion 142 of the hub member 140 and the second end 138 of the needle cannula 134. The bottom cap 193 is then set aside for future use.

Figure 12:
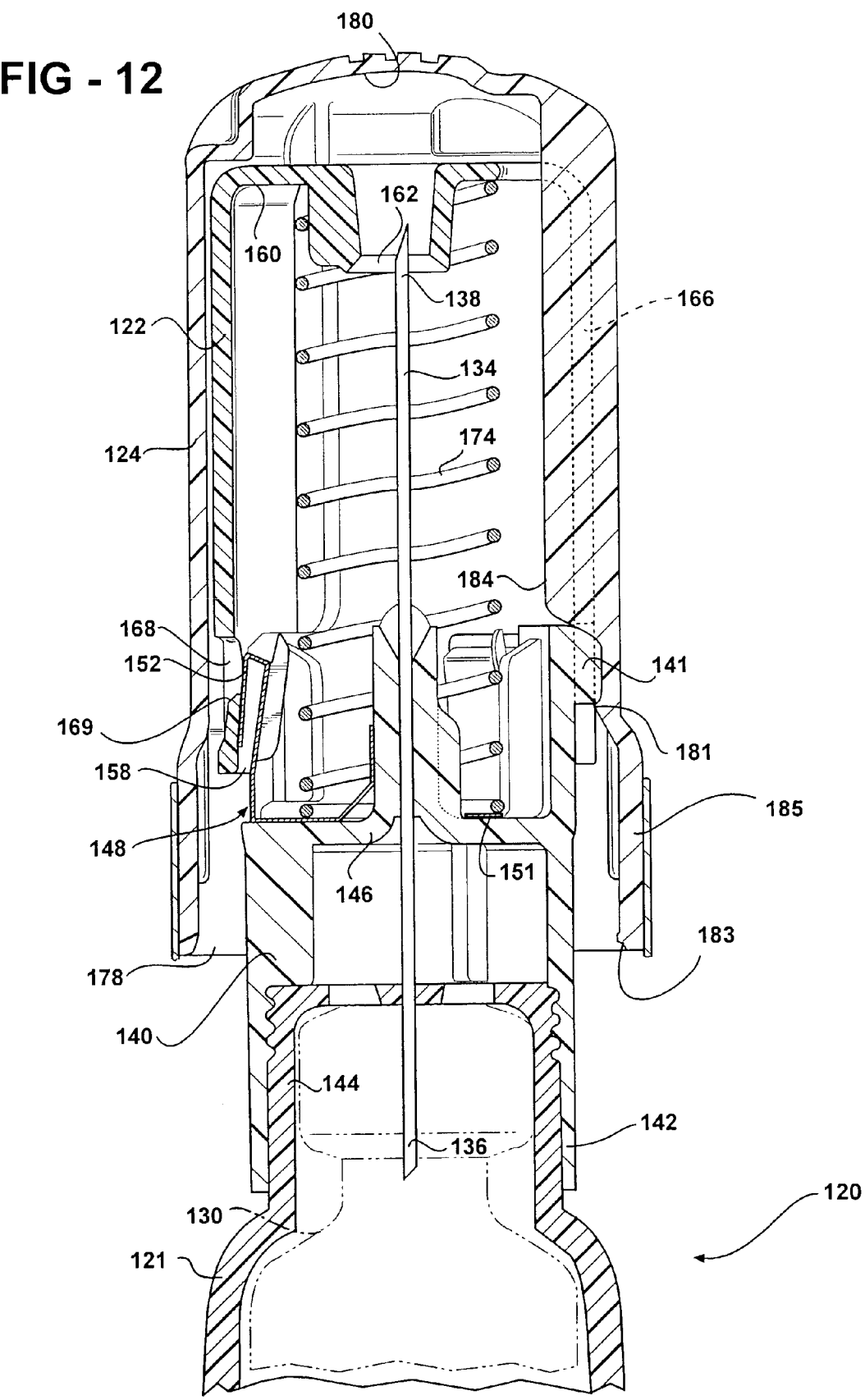
FIG. 12 is a cross-sectional view of the safety shield system of FIG. 9 mounted to a pen injector and with the top cap enclosing the needle assembly.

Referring to FIG. 12, the hub member 140 can now be attached to the pen injector 120 by threading the tubular rim portion 142 of the hub member 140 on the tubular end portion 144 of the pen injector 120. As can be seen from FIG. 12, the internal ribs 184 on the top cap 124, which are aligned with and about the ribs 141 of the hub member 140 and are disposed within the grooves 166 of the shield 122, prevent inadvertent depression or retraction of the shield 122 which could drive the second end 138 of the needle cannula 134 through the opening 168 of the shield 122 and puncture the top cap 124, which would expose the end user to the needle cannula 134. The vial 130 may be previously loaded into the pen injector 120 and the open end may be closed by an end cap (not shown), such that the threading assembly results in piercing the first end 136 of the needle cannula 134 through the closure, such as a rubber septum, in the open end of the vial 130. Alternatively, the vial 130 may be inserted into the pen injector 120 following assembly.

With the needle assembly 123 in place on the pen injector 120, the top cap 124 is removed from the assembly as shown in FIGS. 13-15 and set aside for future use. The needle assembly 123 of the inventive safety shield system 100 is then ready for use.

During use, the patient simply depresses the generally closed end 160 of the shield 122 against a body area to be injected and actuates the pen injector 120. Referring to FIG. 14, this depression moves the shield 122 into the second position and allows the second end 138 of the needle cannula 134 to pass through the opening 168 in the shield 122 such that this end of the needle cannula 134 can be injected into the user.

During the movement of the shield 122 to the second position, the larger fingers 152 slide over the openings 168 and are resiliently biased inwardly. Preferably, the tips 652 of the fingers are longer than the openings 168 to prevent engagement of the finger to the opening during actuation. See, e.g., FIG. 11. Rotation of the shield 122 relative to the hub member 140 is prevented by the ribs 141 which follow the axial slots or grooves 166 assuring axial movement of the shield 122.

Following injection, the needle cannula 134 is withdrawn from the patient and the shield 122 is simultaneously extended by the coil spring 174, such that the second end 138 of the needle cannula 134 is never exposed. Upon full extension of the shield 122 to enclose the second end 138 of the needle cannula 134, the hook-shaped end portions of the fingers 152 engage the chamfers 169 and are received through the openings 168 locking the shield 122 in the extended third position as shown in FIG. 15. That is, the shield 122 cannot be retracted following injection to expose the second end 138 of the needle cannula 134.

The needle assembly 123 may then be removed from the pen injector 120 by unthreading the tubular rim portion 142 of the hub member 140 from the threaded tubular end portion 144 of the pen injector 120. The top 124 and bottom 193 caps can be re-installed over the shield 122 and hub members 140 to completely and safely encompass the needle cannula 134 as shown in FIG. 10. The first end 136 of the needle cannula 134 is thus safely received in the cup-shaped bottom cap 193 and the second end 138 of the needle cannula 134 is protected by the safety shield 122 and the top cap 124. The camming surfaces 197 and 185 interact to self-align the bottom cap and the top cap as they are re-attached to the pen needle. The needle assembly 123 may also be lockingly inserted into the top cap 124 (see, e.g., FIG. 8) to enclose the first end 136 of the needle cannula 134. In that manner, both ends of the needle cannula 134 are lockingly enclosed after use of the needle assembly 123 thereby eliminating the possibility of accidental needle stick injury to the user.

What is claimed is:

1. A safety shield system comprising:
   a needle assembly comprising:
   a hub member;
   a needle cannula carried by said hub member and having sharpened first and second ends;
   a clip member on said hub member and having a plurality of resilient fingers;
   first shielding means having an open end near said first end of said needle cannula, and a generally closed end near said second end of said cannula and having an aperture defined therethrough, said first shielding means being moveably arranged with respect to said hub member between a first position surrounding said needle cannula, a second position exposing a part of said needle cannula, and a third position lockingly surrounding said sharpened second end of said needle cannula; and
   means engaging said first shielding means for biasing said first shielding means toward said first and third positions; and
   second shielding means for lockingly receiving said open end of said first shielding means and enclosing said sharpened first end of said needle cannula.

2. A safety shield system as recited by claim 1, wherein said first shielding means comprises a generally tubular shield.

3. A safety shield system as recited by claim 1, wherein said second shielding means comprises a cap that lockingly receives said open end of said first shielding means.

4. A safety shield system comprising:
   a needle assembly comprising
   a hub member;
   a needle cannula carried by said hub member and having sharpened first and second ends;
   a clip member on said hub member and having a resilient finger;
   first shielding means having an open end near said first end of said needle cannula, and a generally closed end near said second end of said cannula and having an aperture defined therethrough, said first shielding means being moveably arranged with respect to said hub member between a first position surrounding said needle cannula, a second position exposing a part of said needle cannula, and a third position lockingly surrounding said sharpened second end of said needle cannula;
   means engaging said first shielding means for biasing said first shielding means toward said first and third positions; and
   second shielding means for lockingly receiving said open end of said first shielding means and enclosing said sharpened first end of said needle cannula;
   wherein said first shielding means further comprises means for lockingly engaging said resilient finger as said first shielding means is moved from said second position to said third position, and wherein said means for lockingly engaging said resilient finger comprises an opening defined in said first shielding means, said opening being sized and shaped such that said resilient finger passes over said opening as said first shielding means is moved from said first position to said second position, and so as to capture said resilient finger as said first shielding means is moved from said second position to said third position.

5. A safety shield system as recited by claim 4, wherein said clip member comprises a plurality of resilient fingers.

6. A safety shield system as recited by claim 5, wherein said first shielding means comprises a plurality of openings for lockingly engaging said plurality of resilient fingers.

7. A safety shield system as recited by claim 1, wherein said clip member includes a base integrally formed with said resilient fingers.

8. A safety shield system as recited by claim 1, wherein said means for biasing comprises a spring between said hub member and said first shielding means.

9. A safety shield system as recited by claim 1, wherein said second shielding means is sized and shaped to removably receive said generally closed end of said first shielding means, said safety shield system further comprising means for preventing movement of said first shielding means out of said first position when said generally closed end of said first shielding means is removably received by said second shielding means.

10. A safety shield system as recited by claim 9, wherein said means for preventing movement comprises a groove defined in said first shielding means and a rib defined on said second shielding means and disposed in said groove.

11. A safety shield system comprising:
a needle assembly comprising:
a hub member;
a needle cannula carried by said hub member and having sharpened first and second ends;
a clip member on said hub member and having a resilient finger;
first shielding means having an open end near said first end of said needle cannula, and a generally closed end near said second end of said cannula and having an aperture defined therethrough, said first shielding means being moveably arranged with respect to said hub member between a first position surrounding said needle cannula, a second position exposing a part of said needle cannula, and a third position lockingly surrounding said sharpened second end of said needle cannula;
means engaging said first shielding means for biasing said first shielding means toward said first and third positions; and
second shielding means for lockingly receiving said open end of said first shielding means and enclosing said sharpened first end of said needle cannula; and
means for preventing rotation between said hub member and said first shielding means, wherein said means for preventing rotation comprises a plurality of radially spaced grooves defined in said first shielding means and a plurality of radially spaced ribs defined on said hub member.

12. A safety shield system comprising:
a needle assembly comprising:
a hub member;
a needle cannula carried by said hub member and having sharpened first and second ends;
a clip member on said hub member and having a resilient finger;
a tubular shield having an open end near said first end of said needle cannula, and a generally closed end near said second end of said needle cannula, said generally closed end having an aperture defined therethrough, said tubular shield being moveably arranged with respect to said hub member between a first position surrounding said needle cannula, a second position exposing a part of said needle cannula, and a third position lockingly surrounding said sharpened second end of said needle cannula; and
a spring for biasing said tubular shield toward said first and third positions; and
a first cap to lockingly receive said open end of said tubular shield to lockingly enclose said sharpened first end of said needle cannula,
wherein said first cap is sized and shaped to removably receive said generally closed end of said tubular shield, and
further comprising means for preventing movement of said tubular shield out of said first position when said generally closed end of said tubular shield is removably received by said first cap,
wherein said means for preventing movement comprises a groove defined in said tubular shield and a rib defined on said first cap and disposed in said groove.

13. A safety shield system as recited by claim 12, wherein said tubular shield further comprises an opening defined in a sidewall for lockingly engaging said resilient finger as said tubular shield is moved from said second position to said third position.

14. An injection system comprising:
a pen injector having means for receiving a needle assembly;
a needle assembly removably securable to said pen injector and comprising:
a hub member complementarily sized and shaped with said receiving means of said pen injector for removably securing said needle assembly to said pen injector; a needle cannula carried by said hub member and having sharpened first and second ends;
a clip member on said hub member and having a resilient finger;
first shielding means having an open end near said first end of said needle cannula, and a generally closed end near said second end of said cannula and having an aperture defined therethrough, said first shielding means being moveably arranged with respect to said hub member between a first position surrounding said needle cannula, a second position exposing a part of said needle cannula, and a third position lockingly surrounding said sharpened second end of said needle cannula; and means engaging said first shielding means for biasing said first shielding means toward said first and third positions; and second shielding means for lockingly receiving said open end of said first shielding means and enclosing said sharpened first end of said needle cannula after said needle assembly is removed from said pen injector.

* * * * *